United States Patent

Vorbrueggen et al.

Patent Number: 5,124,343
Date of Patent: Jun. 23, 1992

[54] CARBACYCLINS, PROCESS FOR THE PREPARATION THEREOF, AND USE THEREOF AS MEDICINAL AGENTS

[75] Inventors: Helmut Vorbrueggen; Hernd Raduechel; Werner Skubulla; Norbert Schwarz, all of Berlin; Jorge Casals-Stenzel, Mainz; Gerda Mannesmann, Cologne; Michael H. Town, Berlin, all of Fed. Rep. of Germany

[73] Assignee: Schering Aktiengesellschaft, Berlin & Bergkamen, Fed. Rep. of Germany

[21] Appl. No.: 141,233

[22] Filed: Jan. 6, 1988

Related U.S. Application Data

[63] Continuation of Ser. No. 25,254, Mar. 12, 1987, abandoned, which is a continuation of Ser. No. 804,199, Dec. 3, 1985, abandoned, which is a continuation of Ser. No. 558,419, filed as PCT/DE83/00045, Mar. 11, 1983, abandoned.

[30] Foreign Application Priority Data

Feb. 18, 1983 [DE] Fed. Rep. of Germany ....... 3306125

[51] Int. Cl.$^5$ .................. C07C 177/00; A61K 31/557
[52] U.S. Cl. .................... 514/374; 514/530; 514/573; 514/601; 514/616; 514/729; 548/237; 560/116; 562/498; 564/98; 564/152; 568/819
[58] Field of Search .............. 560/119, 116; 562/501, 562/498

[56] References Cited

U.S. PATENT DOCUMENTS

| | | | |
|---|---|---|---|
| 4,405,468 | 8/1977 | Kurono et al. | |
| 4,423,067 | 12/1983 | Skubulla | 560/119 |
| 4,692,464 | 9/1987 | Skuballa et al. | 560/121 |

FOREIGN PATENT DOCUMENTS 2013661 8/1979 United Kingdom .

OTHER PUBLICATIONS

Prostaglandings; November 1981, vol. 22, No. 5, pp. 809–830.

Primary Examiner—Robert Gerstl
Attorney, Agent, or Firm—Millen, White & Zelano

[57] ABSTRACT

The invention relates to carbacyclins of general Formula I

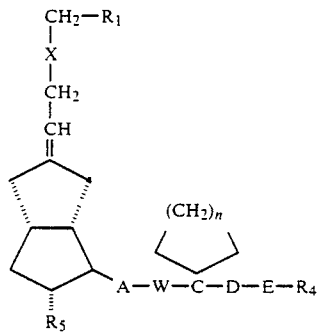

wherein
$R_1$ is the residue $CH_2OH$ or

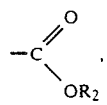

with $R_2$ meaning a hydrogen atom, an alkyl, cycloalkyl, aryl residue, a

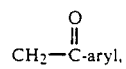

or heterocyclic residue, or
$R_1$ is the residue

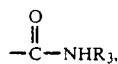

with $R_3$ meaning an alkanoyl or alkanesulfonyl residue of respectively 1–10 carbon atoms or the residue $R_2$, or
$R_1$ is the residue

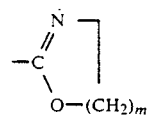

wherein m is the number 1 or 2,
X is an oxygen atom or a $CH_2$-group,
A is a trans—CH=CH— or —≡C—group,
W is a free or functionally modified hydroxymethylene group wherein the OH-group can be in the α- or β-position, n is the number 1, 2, or 3, D is a straight-chain alkylene group of 1-5 carbon atoms, E is a —C≡C—-bond or a —CR$_6$=CR$_7$—group wherein R$_6$ and R$_7$ are different from each other and mean a hydrogen atom or an alkyl group of 1-5 carbon atoms or a hydrogen atom or a halogen atom, preferably chlorine, R$_4$ is an alkyl, cycloalkyl, or optionally substituted arly group, or a heterocyclic group, R$_5$ is a free or functionally modified hydroxy group, and if R$_2$ means a hydrogen atom, the salts thereof with physiologically compatible bases;

to processes for the preparation thereof, and to the use thereof as blood-pressure-lowering agents.

23 Claims, No Drawings

CARBACYCLINS, PROCESS FOR THE PREPARATION THEREOF, AND USE THEREOF AS MEDICINAL AGENTS

This is a continuation of application Ser. No. 025,254, filed Mar. 12, 1987, abandoned, which is a continuation of Ser. No. 804,199, filed Dec. 3, 1985, abandoned, which is a continuation of Ser. No. 558,419, filed Nov. 14, 1983, abandoned, which is the National Phase application of International Application No. PCT/DE83/0045, filed Mar. 11, 1983.

The invention relates to novel prostacyclin derivatives, a process for the preparation thereof, as well as use thereof as medicinal agents.

(5E)- and (5Z)-6a-carbaprostaglandin $I_2$ analogs are disclosed in German Unexamined Laid-Open Applications DOS's Nos. 2,845,770; 2,900,352; 2,902,442; 2,904,655; 2,909,088; and 2,912,409. The nomenclature of the compounds of this invention is based on a proposal by Morton and Brokaw (J. Org. Chem. 44 : 2880 [1979]). The synthesis of these compounds yields in all cases two double-bond isomers characterized by the addition (5E) or (5Z). The two isomers of this prototype are clarified by the following structural formulae:

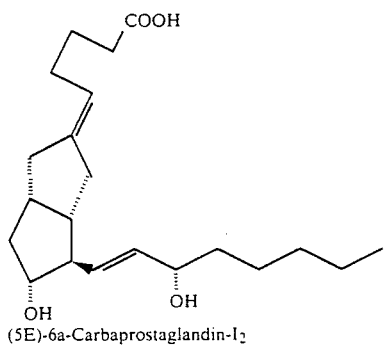
(5E)-6a-Carbaprostaglandin-$I_2$

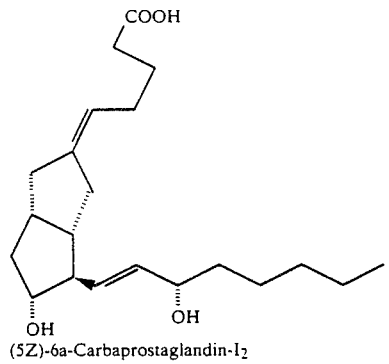
(5Z)-6a-Carbaprostaglandin-$I_2$

It is known from the very voluminous state of the art of prostacyclines and their analogs that this class of compounds is studied, due to biological and pharmacological properties, for the treatment of mammals, including man. The use of these compounds as medicinal agents, however, frequently meets with difficulties since their period of effectiveness is too short for therapeutic purposes. All structural modifications serve the purpose of increasing the duration of effectiveness as well as the selectivity of efficacy.

It has now been found that longer duration of effectiveness, higher selectivity, and improved efficacy can be obtained by the introduction of a cycloalkyl group in the 16-position of the carbacyclin. The compounds of this invention have blood-pressure-lowering and bronchodilatory effects. They are furthermore suitable for inhibition of thrombocyte aggregation, vasodilation, and inhibition of gastric acid secretion.

The invention relates to carbacyclin derivatives of general Formula I

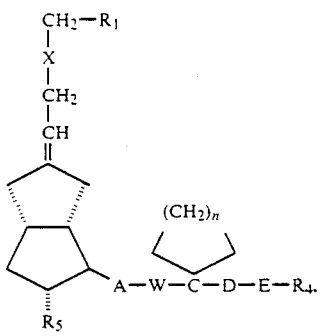

wherein
$R_1$ is the residue $CH_2OH$ or

with $R_2$ meaning a hydrogen atom, an alkyl, cycloalkyl, aryl residue, a

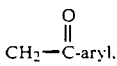

or heterocyclic residue, or
$R_1$ is the residue

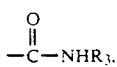

with $R_3$ meaning an alkanoyl or alkanesulfonyl residue of respectively 1–10 carbon atoms, or the residue $R_2$, or
$R_1$ is the residue

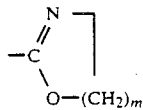

wherein m is the number 1 or 2,
X is an oxygen atom or a $CH_2$-group,
A is a trans-CH=CH— or —C≡C-group,
W is a free or functionally modified hydroxy-methylene group wherein the OH-group can be in the α- or β-position,
n is the number 1,2, or 3,
D is a straight-chain alkylene group of 1–5 carbon atoms,
E is a —C≡C-bond or a —$CR_6$=$C_7$-group wherein $R_6$ and $R_7$ are different from each other and mean a hydrogen atom or an alkyl group of 1–5 carbon atoms or a hydrogen atom or a halogen atom, preferably chlorine, $R_4$ is an alkyl, cycloalkyl, or optionally substituted aryl group, or a heterocyclic group, $R_5$ is a free or functionally modified hydroxy group, and, if $R_2$ means a hydrogen atom, the salts thereof with physiologically compatible bases.

The compounds of Formula I represent (5E)- as well as (5Z)-isomers.

Alkyl groups $R_2$ can be straight- or branched-chain alkyl groups of 1-10 carbon atoms, e.g. methyl, ethyl, propyl, isopropyl, butyl, isobutyl, tert-butyl, pentyl, isopentyl, neopentyl, heptyl, hexyl, decyl.

The alkyl groups $R_2$ can optionally be mono- to polysubstituted by halogen atoms, $C_1$-$C_4$-alkoxy groups, optionally substituted $C_6$-$C_{10}$-aryl groups, di-$C_1$-$C_4$-alkylamines, and tri-$C_1$-$C_4$-alkylammonium. Monosubstituted alkyl groups are preferred. Examples for substituents are fluorine, chlorine, or bromine atoms, phenyl, dimethylamino, diethylamino, methoxy, ethoxy.

Preferred alkyl groups $R_2$ are those of 1-7 carbon atoms, e.g. methyl, ethyl, propyl, dimethylaminopropyl, isobutyl, butyl. Especially preferred alkyl groups $R_2$ are those of 1-4 carbon atoms. Aryl groups $R_2$ can be substituted as well as unsubstituted aryl groups, for example phenyl, 1-naphthyl, and 2-naphthyl, each of which can be substituted by 1-3 halogen atoms, a phenyl group, 1-3 alkyl groups or respectively 1-4 carbon atoms, by chloromethyl, fluoromethyl, trifluoromethyl, carboxy, hydroxy, or alkoxy groups of 1-4 carbon atoms. Preferred are the substituents in the 3- and 4-positions on the phenyl ring, for example by fluorine, chlorine, alkoxy, or trifluoromethyl, or in the 4-position by hydroxy. The cycloalkyl group $R_2$ can contain in the ring 4-10, preferably 5 and 6 carbon atoms. The rings can be substituted by alkyl groups of 1-4 carbon atoms. Examples that can be cited are cyclopentyl, cyclohexyl, methylcyclohyexyl, and adamantyl. Suitable heterocyclic groups $R_2$ are 5- and 6-membered heretocycles containing at least one hetero atom, preferably nitrogen, oxygen, or sulfur. Examples are 2-furyl, 3-furyl, 2-thienyl, 3-thienyl, 2-pyridyl, 3-pyridyl, 4-pyridyl, and others. The aryl residue in the

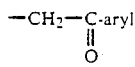

group of $R_2$ can be phenyl, α- or β-naphthyl, which can be substituted by 1-3 phenyl groups, which latter, in turn, can be substituted by 1-3 halogen atoms, such as F, Cl, or Br, or 1-3 $C_1$-$C_4$-alkoxy groups or 1-3 halogen atoms (F, Cl, Br). Single substitutions by phenyl, $C_1$-$C_2$-alkoxy, chlorine, or bromine are preferred.

Suitable acid residues $R_3$ can be physiologically compatible acid residues. Preferred acids are organic carboxylic acids and sulfonic acids of 1-15 carbon atoms pertaining to the aliphatic, cycloaliphatic, aromatic, aromatic-aliphatic, and heterocyclic series. These acids can be saturated, unsaturated and/or polybasic and/or substituted in the usual way. Examples for substituents are $C_1$-$C_4$-alkyl, hydroxy, $C_1$-$C_4$-alkoxy, oxo, or amino groups, or halogen atoms (F, Cl, Br).

The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentalectic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloracetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid. Especially preferred acyl residues are considered to be those of up to 10 carbon atoms. Examples for sulfonic acids are methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid pyrrolidino-, piperidino-, pieperazine-, N-methylpiperazine-, and morpholinosulfonic acids.

The hydroxy groups $R_5$ and those in W can be functionally modified, for example by etherification or esterification, wherein the free or modified hydroxy groups in W can be in the α- or β-position, free hydroxy groups being preferred.

Suitable ether and acyl residues are those known to persons skilled in the art. Ether residues that can be easily split off are preferred, e.g. the tetrahydropyranyl, tetrahyrofuranyl, α-ethoxyethyl, trimethylsilyl, dimethyl-tert-butylsilyl, and tri-p-benzylsilyl residues. Acyl residues can be the same as mentioned for $R_3$; worth citing by name are, for example, acetyl, propionyl, butyryl, benzoyl.

Suitable for the alkyl group $R_4$ are straight- and branched-chain, saturated and unsaturated alkyl residues, preferably saturated ones, of 1-10, especially 1-7 carbon atoms which can optically be substituted by optionally substituted aryl. Examples are methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

The cycloalkyl group $R_4$ can contain in the ring 4-10, preferably 5 and 6 carbon atoms. The rings can be substituted by alkyl groups of 1-4 carbon atoms. Examples are cyclopentyl, cyclohexyl, methylcyclohexyl, and adamantyl.

Examples for substituted and unsubstituted aryl groups $R_4$, respectively, are: phenyl, 1-naphthyl, and 2-naphthyl, each of which can be substituted by 1-3 halogen atoms, a phenyl group, 1-3 alkyl groups of respectively 1-4 carbon atoms, a chloromethyl, fluoromethyl, trifluoromethyl, carboxy, $C_1$-$C_4$-alkoxy, or hydroxy group. Substitution in the 3- and 4-positions on the phenyl ring is preferred, for example by fluorine, chlorine, $C_1$-$C_4$-alkoxy, or trifluoromethyl, or in the 4-position by hydroxy. Suitable heterocyclic groups $R_4$ are 5- and 6-membered heretocycles containing at least one hetero atom, preferably nitrogen, oxygen, or sulfur. Examples are 2-furyl, 2-thienyl, 2-pyridyl, 3-pyridyl, 4-pyridyl, 3-furyl, 3-thienyl, etc.

Suitable as the alkylene group D are straight-chain alkylene residues of 1-5 carbon atoms, such as, for example, methylene, ethylene, propylene, tetra- or pentamethylene.

Inorganic and organic bases are suitable for salt formation with the free acids ($R_2 = H$), as they are known to those skilled in the art for the formation of physiologically compatible salts. Examples are: alkali hydroxides, such as sodium and potassium hydroxide, alkaline earth hydroxides, such as calcium hydroxide, ammonia, amines, such as ethanolamine, diethanolamine, triethanolaine, N-methylglucamine, morpholine, tris(hydroxymethyl)methylamine, etc.

The invention furthermore relates to a process for the preparation of carbacyclin derivatives of general Formula I, characterized in that (a) a compound of general Formula II

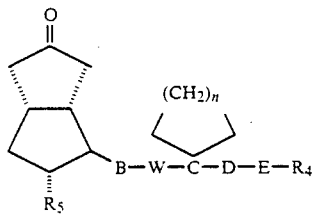

II wherein
$R_5$, W, n, D, E and $R_4$ have the meanings set forth above, and
B is a trans-double bond or a —CH=CBr-group, is reacted, if desired after blockage of any free hydroxy groups present, with a Wittig reagent of Formula III

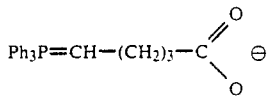

III or (b) a compound of general Formula IV

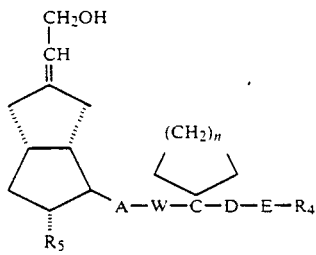

IV wherein $R_4$, $R_5$, A, W, D, E, n have the above-indicated meanings,
is etherified, in the presence of a base, optionally after blockage of any free hydroxy groups present, with a haloacetic acid derivative of general Formula V

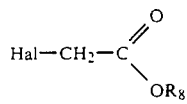

V wherein
Hal is a chlorine, bromine, or iodine atom, and
$R_8$ is an alkyl residue or a trialkylsilyl residue with $C_1$-$C_4$-alkyl groups, or an alkali metal (Na, Li, K), and, in the process products obtained according to (a) or (b), thereafter, if desired, in any arbitrary sequence, isomers are separated and/or blocked hydroxy groups are liberated and/or free hydroxy groups are esterified or etherified and/or a free carboxy group is esterified and/or an esterified carboxy group is saponified or a carboxy group is converted into an amide or, with a physiologically compatible base, into a salt.

The reaction of the compound of general Formula II with the Wittig reagent of Formula III, obtained from the corresponding phosphonium salt with methanesulfinylmethyl sodium or methanesulfinyl potassium, or potassium tert-butylate in dimethyl sulfoxide or dimethyl sulfoxide-tetrahydrofuran mixtures, is conducted at temperatures of 0° C. to 100° C., preferably 20° C.-60° C., in an aprotic solvent or solvent mixture, preferably dimethyl sulfoxide, dimethylformamide, or tetrahydrofuran. The thus-produced Z- and E-configured olefins (5,6-position) are separated in the usual way, for example by column or layer chromatography. If B is a —CH=CBr-group, the 13,14-acetylene bond is formed simultaneously during the above-described Wittig olefin-producing reaction, with hydrogen bromide being split off.

The compound of general Formula IV is reacted with a haloacetic acid derivative of general Formula V at temperatures of 0° C.-100° C., preferably 10° C.-80° C., in an aprotic solvent or solvent mixture, for example dimethyl sulfoxide, dimethylformamide, tetrahydrofuran, etc. Suitable bases are those known to persons skilled in the art for etherification reactions, for example, sodium hydride, potassium tert-butylate, butyllithium, etc.

The saponification of the carbacyclin esters is effected according to methods known to those skilled in the art, such as, for example, with alkaline catalysts.

The ester group $COOR_2$, wherein $R_2$ is an alkly group of 1-10 carbon atoms, is introduced for $R_1$ according to methods known to persons skilled in the art. The carboxy compounds are reacted, for example, with diazo hydrocarbons in a conventional process. The esterification with diazo hydrocarbons is conducted, for example, by mixing a solution of the diazo hydrocarbon in an inert solvent, preferably in diethyl ether, with the carboxy compound in the same or in another inert solvent, e.g. methylene chloride. After the reaction has been completed within 1-30 minutes, the solvent is removed and the ester purified as usual. Diazoalkanes are either known or can be produced according to known methods [Org. Reactions 8 : 389-394 (1954)].

The instruction of the ester group $COOR_2$, wherein $R_2$ is a substituted or unsubstituted aryl group, for $R_1$ takes place according to methods known to persons skilled in the art. For example, the carboxy compounds and the corresponding arylhydroxy compounds are reacted with dicyclohexylcarbodiimide in an inert solvent, in the presence of a suitable base, for example pyridine or triethylamine. Suitable solvents are methylene chloride, ethylene chloride, chloroform, ethyl acetate, tetrahydrofuran, preferably chloroform. The reaction is carried out at temperatures of between −30° C. and +50° C., preferably at +10° C.

The introduction of the ester group —$COOR_2$ for $R_1$ can also take place by reacting the carboxylate anion with the corresponding alkyl halogenide or haloketone

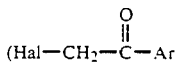

wherein Ar is phenyl, diphenyl, both of which can be substituted by $C_1-C_2$-alkoxy or chlorine or bromine).

The $\Delta^2$-oxazoline group

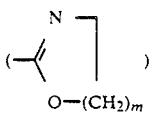

is introduced for $R_1$ according to the processes described in DOS's 3,047,759; 3,115,997; and 3,145,830. For example, the carboxy compounds are converted into the $\Delta^2$-oxazalines in the presence of the corresponding amino alcohol with tert-phosphines, especially triphenylphosphine, in the presence of halogen compounds such as, in particular, carbon tetrachloride, and in the presence of a tertiary base, preferably triethylamine or DBN.

The carbacyclin derivatives of general Formula I wherein $R_1$ is a carboxy group ($R_2=H$) can be converted into the salts with suitable amounts of the corresponding inorganic bases, under neutralization. For example, by dissolving the corresponding acids in water containing the stoichiometric quantity of the base, the solid inorganic salt is obtained after evaporation of the water or after adding a water-miscible solvent, e.g. alcohol or acetone.

The amine salts are prepared as usual. For this purpose, the carbacyclin acid is dissolved, for example, in a suitable solvent, such as ethanol, acetone, diethyl ether, or benzene, and at least the stoichiometric amount of the amine is added to this solution. During this procedure, the salt is ordinarily obtained in the solid form or is isolated as usual after evaporation of the solvent.

The functional modification of the free OH-groups takes place according to methods known to persons skilled in the art. For example, in order to introduce the ether blocking groups, the reaction is conducted with dihydropyran in methylene chloride or chloroform with the use of an acidic condensation agent, for example p-toluenesulfonic acid. The dihydropyran is used in excess, preferably in four to ten times the amount required theoretically. The reaction is normally completed at 0° C.-30° C. after 15-30 minutes.

The acyl blocking groups are introduced by conventionally reacting a compound of general Formula I with a carboxylic acid derivative, for example an acid chloride, acid anhydride, etc.

The liberation of a functionally modified OH-group to obtain the compounds of general Formula I takes place by methods known per se. For example, ether blocking groups are split off in an aqueous solution of an organic acid, such as, for example, acetic acid, propionic acid, etc., or in an aqueous solution of an organic acid, e.g. hydrochloric acid. In order to improve solubility, a water-miscible, inert organic solvent is suitably added. Suitable organic solvents are, for example, alcohols, such as methanol and ethanol, and ethers, such as dimethoxyethane, dioxane, and tetrahydrofuran. Tetrahydrofuran is preferably employed. The splitting-off step is conducted preferably at temperatures of between 20° C. and 80° C.

The silyl ether blocking groups are split off, for example, with tetrabutylammonium flouride. Examples for suitable solvents are tetrahydrofuran, diethyl ether, dioxane, methylene chloride, etc. The splitting-off step is preferably conducted at temperatures of between 0° C. and 80° C.

The alkali groups are saponified, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Alkali carbonates and hydroxides that can be mentioned are potassium and sodium salts, but the potassium salts are preferred. Suitable alkaline earth carbonates and hydroxides are, for example, calcium carbonate, calcium hydroxide, and barium carbonate. The reaction takes place at $-10°$ C. to 70° C., preferably at 25° C.

The amide group

for $R_1$ is introduced according to methods known to those skilled in the art. The carboxylic acids of general Formula I ($R_2=H$) are first of all converted into the mixed anhydride with the isobutyl ester of chloroformic acid, in the presence of a tertiary amine, e.g. triethylamine. The mixed anhydride is reacted with the alkali salt of the corresponding amide or with ammonia ($R_3=H$) in an inert solvent or solvent mixture, e.g. tetrahydrofuran, dimethoxyethane, dimethylformamide, hexamethylphosphoric triamide, at temperatures of between $-30°$ C. and $+60°$ C., preferably at 0° C.-30° C.

Another possibility for introducing the amide group $-CONHR_3$ for $R_1$ resides in reacting a 1-carboxylic acid of general Formula I ($R_2=H$) wherein free hydroxy groups are optionally blocked intermediarily, with compounds of general Formula VI

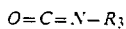             VI wherein $R_3$ has the meanings given above.

The reaction of the compounds of general Formula I ($R_1=COOH$) with an isocyanate of general Formula VI takes place, if desired, with the addition of a tertiary amine, such as, for example, triethylamine or pyridine. The reaction can be accomplished without a solvent or in an inert solvent, preferably acetonitrile, tetrahydrofuran, acetone, dimethylacetamide, methylene chloride, diethyl ether, toluene, at temperatures of between $-80°$ C. and 100° C., preferably at 0° C.-30° C.

If the starting compound contains OH-groups in the prostane residue, these OH-groups are also made to react. If, in the final analysis, end products are desired containing free hydroxy groups in the prostane moiety, then starting compounds are suitably employed wherein these are blocked intermediarily by preferably readily cleavable ether or acyl residues.

The starting of general Formulae II and IV serving as the starting material can be prepared, for example, by reacting conventionally an aldehyde of Formula VII (DOS 2,845,770)

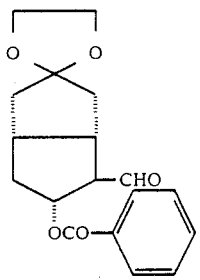

with a phosphonate of general Formula VIII

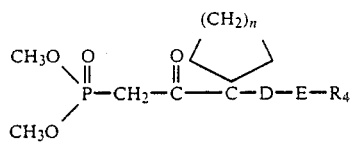

wherein D, E, and R₄ have the meanings given above, in the presence of a deprotonating agent, e.g., sodium hydride or potassium tert-butylate, to obtain a ketone of general Formula IX (X=H) or additionally, in the presence of a brominating agent, for example N-bromosuccnimide, to a ketone of general Formula IX (X=Br)

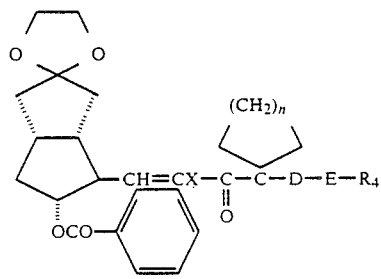

After reduction of the keto group with zinc borohydride or sodium borohydride or reaction with alkyl magnesium bromide or alkyl lithium and subsequent separation of epimers, the compounds of general Formula X are obtained

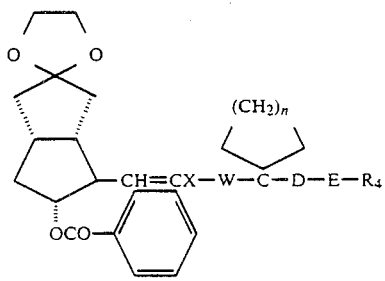

By saponification of the ester group, for example with potassium carbonate in menthol, as well as optically hydrogenation of the double bond or, if desired, etherification with dihydropyran and subsequent splitting off of hydrogen bromide with, for example, potassium tert-butylate in dimethyl sulfoxide, ketal splitting with aqueous acetic acid, as well as optically functional modification of the free hydroxy groups, for example by etherification with dihydropyran, the ketone of general Formula XI is obtained

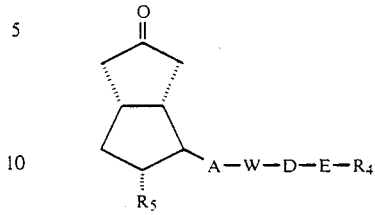

After olefin-forming reaction with phosphonoacetic acid triethyl ester or phosphonoacetic acid trimethyl ester and subsequent reduction with lithium aluminum hydride, the compounds of general Formula IV isomeric in the double bond are obtained, which can optically be separated.

After reduction of the keto group with sodium borohydride and optically separation of epimers, saponification of the ester group, for example with potassium carbonate in methanol, and ketal splitting with aqueous acetic acid, as well as separation of epimers, if desired, the ketone of general Formula XII is obtained

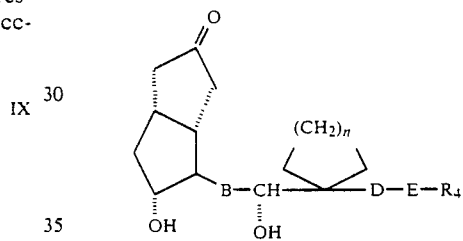

Etherification of the hydroxy groups with, for example, dihydropyran, in the presence of catalytic amounts of p-toluenesulfonic acid yields the compounds of general Formula II.

The phosphonate of general Formula VIII are prepared conventionally by reacting an ester of general Formula XIII

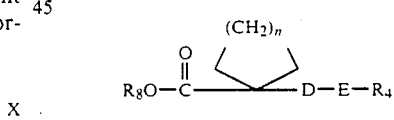

wherein
  N, D, E, and R₄ have the meanings given above and R₈ is an alkly group of 1-5 carbon atoms, with the anion of methylphosphonic acid dimethyl ester.

The esters of general Formula XIII are produced in a conventional way by reacting a dianion XIV with a halogen compound XV, wherein n, D, E, R₄ have the above-cited meanings and Hal is a chlorine, bromine, or iodine atom.

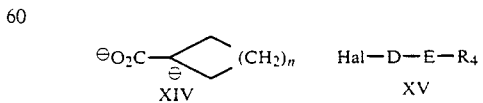

The compounds of this invention have blood-pressure-lowering and bronchodilatory effects. They are furthermore suitable for inhibiting thrombocyte aggregation. Consequently, the novel carbacyclin derivatives of Formula I represent valuable pharmaceutically active agents. Moreover, with a similar spectrum of activity, they exhibit, as compared with corresponding prostaglandins, higher specificity and, above all, substantially longer efficacy. As compared with PGI$_2$, they are distinguished by higher stability. The high tissue specificity of the novel prostaglandins is demonstrated in a study on smooth-muscle organs, such as, for example, on the guinea pig ileum or on the isolated rabbit trachea, where a substantially lower stimulation can be observed that in the administration of natural prostaglandins of the E-, A-, or F-type.

The novel carbacyclin analogs exhibit the properties typical for prostacyclines, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, antiallergic properties, lowering of pulmonary vascular resistance and pulmonary pressure, promotion of kidney blood flow, utilization in place of heparin or as adjuvant in dialysis of hemofiltration, preservation of blood plasma stores, especially blood platelet stores, inhibition of labor, treatment of gestational toxicosis, enhancement of cerebral blood flow, etc. Besides, the novel carbacyclin derivatives exhibit antiproliferative and antidiarrheogenic properties. The carbacyclins of this invention also can be utilized in combination, for example, with β-blockers or diuretics.

The dosage of the compounds is 1–1,500 μg/kg/day if administered to human patients. The unit dosage for the pharmaceutically acceptable carrier is 0.01–100 mg.

With intravenous injection administered to non-anesthetized, hypertonic rats in doses of 5, 20, and 100 μg/kg body weight, the compounds of this invention exhibit a stronger blood-pressure-lowering effect and a more prolonged duration of efficacy than PGE$_2$ and PGA$_2$ without triggering diarrhea, as does PGE$_2$, or cardiac arrhythmias, as does PGA$_2$.

Upon intravenous injection administered to narcotized rabbits, the compounds of this invention show, as compared with PGE$_2$ and PGA$_2$, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees, or capsules.

The invention accordingly also concerns medicinal agents based on the compounds of general Formula I and conventional auxiliary agents and excipients.

The active agents of this invention are to serve, in conjunction with the auxiliary agents known and customary in galenic pharmacy, for example for the preparation of blood-pressure-lowering agents.

EXAMPLE 1

(5E)-18,18,19,19-Tetradehydro-16,16-trimethylene-6a-carbaprostaglandin I$_2$

At 5° C., 4.74 g of potassium tert-butylate is added within 45 minutes to a solution of 9.36 g of 4-carboxybutyltriphenylphosphonium bromide in 20 ml of dimethyl sulfoxide and 8 ml of tetrahydrofuran, and the mixture is agitated for another 45 minutes at 5° C. To the red ylene solution is added a solution of 1.65 g of (1R,5S,6R,7R)-7-(tetrahydropyran-2-yloxy)-6-[(E)-(3R)-3-(tetrahydropryan-2-yloxy)-4,4-trimethylenecotlen-6-ynyl]bicyclo[3.3.0]octan-3-one in 2 ml of tetrahydrofuran, and the mixture is agitated for 3 hours at 35° C. The reaction mixture is poured on ice water, acidified to pH 4 with citric acid, and extracted with methylene chloride. The organic phase is shaken with brine, dried over magnesium sulfate, and evaporated under vacuum. The residue is purified by chromatography. With hexane/ethyl acetate (1+1), 280 mg of the Z-configured olefin is first of all obtained, and, as the more polar component, 700 mg of (5E)-18,18,19,19-tetradehydro-16,16-trimethylene-6a-carbaprostaglandin I$_2$ 11,15-bis(tetrahydropyranyl ether) as a colorless oil.

IR (CHCl$_3$): 3520, 2940, 2860, 1710, 1073, 1019, 972 cm$^{-1}$.

In order to cleave the blocking groups, 650 mg of the above-obtained product is stirred with 20 ml of a mixture of acetic acid/water/tetrahydrofuran (65/35/10) at 25° C. for 24 hours, evaporated under vacuum, and the residue chromatographed on silica gel. With ethyl acetate/0.1% acetic acid, 320 mg of the title compound is produced as a colorless oil.

IR: 3600, 3520, 3410 (broad), 2937, 2860, 1710, 972 cm$^{-1}$.

1(a) 2-Oxo-3,3-trimethylenehept-5-ynephosphonic Acid Dimethyl Ester

At −30° C., 265 ml of 1.66-molar butyllithium solution in hexane is added to a solution of 44.52 g of diisopropylamine in 200 ml of tetrahydrofuran, and thereafter 20.02 g of cyclohexanecarboxylic acid is added thereto. The mixture is stirred for 30 minutes at −10° C. and then 31.92 g of 1-bromo-2-butyne is added dropwise and the mixture is agitated for 16 hours at 25° C. whereupon it is poured on 600 ml of ice water. After acidifying with 2N hydrochloric acid to pH 4, the mixture is extracted with ether, the extract is washed with brine, dried over magnesium sulfate, and the the evaporated under vacuum. The residue is purified by distillation, thus obtaining 18 g of 2,2-trimethylenehex-4-ynoic acid (bp 140° C.-143° C., 15 torr).

IR: 3520, 2985, 2961, 1700, 1425, 1408, 1100, 1035, 920, 880 cm$^{-1}$.

For esterification, 14 g of the thus-produced carboxylic acid is refluxed in 200 ml of methanol and 2 ml of concentrated sulfuric acid for 6 hours, then cooled, poured on 150 g of ice, and extracted with ether. The extract is washed with soda solution and brine, dried over magnesium sulfate, and the ether is evaporated under vacuum. After distillation (bp 92° C.-94° C. at 15 torr), 13 g of 2,2-trimethylenehex-4-ynoic acid methyl ester is obtained.

IR: 2985, 2951, 292L, 2858, 1725, 1431, 1330, 1099, 978, 875 cm$^{-1}$.

At −70° C., 200 ml of 1.7-molar butyllithium solution in hexane is added dropwise to a solution of 21.35 g of methanephosphonic acid dimethyl ester in 300 ml of tetrahydrofuran. After 20 minutes, a solution of 13 g of the above-produced ester in 50 ml of tetrahydrofuran is added dropwise to the reaction mixture and the latter stirred for another 5 hours at −70° C. Then the mixture is combined with 12 ml of acetic acid and exhaustively evaporated under vacuum. The residue is dissolved with 50 ml of water and repeatedly extracted with dichloromethane, dried over magnesium sulfate, and evaporated under vacuum. After distillation of the reside (bp 133° C.-139° C. at 0.5 torr), 15.1 g of the title compound is obtained as a colorless liquid.

IR: 3420 (broad), 2988, 2952, 2850, 1702, 1251 1030 cm$^{-1}$.

1(b)
(1R,5S,6R,7R)-3,3-Ethylenedioxy-7-benzoyloxy-6-[(E)-3-oxo-4,4-trimethylene-oct-1-en-6-ynyl]bicyclo[3.3.0]octane At 0° C., a solution of 11.62 of the phosphonate produced according to Example 1(a) in 120 ml of dimethoxyane is added dropwise to a suspension of 980 mg of sodium hydride in 200 ml of dimethoxyethane, and the mixture is stirred for one hour at 0° C. Then a solution of 11.40 g of (1R,5S,6R,7R)-3,3-ethylenedioxy-7-benzoyloxy-6-6-formylbicyclo[3.3.0]octane in 120 ml of dimethoxyethane is introduced dropwise. After 2 hours at 0° C., the mixture is poured on 800 ml of saturated ammonium chloride solution and extracted with ether, the extract washed with brine, dried over magnesium sulfate, and evaporated under vacuum. Chromatography of the residue on silica gel with hexane/ ether (1 + 1) yields 9.10 g of the title compound as a colorless oil.

IR: 2940, 2859, 1712, 1686, 1621, 1600, 1584, 1270, 980, 942 cm$^{-1}$.

1(c)
(1R,5S,6R,7R)-3,3-Ethylenedioxy-7-benzoyloxy-6-[(E)-(3R)-3-hydroxy-4,4-trimethyleneoct-1-en-6-ynyl]bicyclo[3.3.0]octane A solution of 8.10 of the ketone prepared according to Example 1(b) in 200 of methane is combined at −40° C. with 3.60 g of sodium borohydride. The mixture is then stirred for 30 minutes at −40° C., diluted thereafter with 2 l of ether, shaken repeatedly with respectively 50 ml of brine, dried over magnesium sulfate, and evaporated under vacuum. The residue is purified by chromatography on silica gel with ether/hexane (7 + 3), thus obtaining 4.9 g of the title compound as a colorless oil.

IR: 3600, 3520, 2938, 2881, 1713, 1601, 1586, 1275, 970, 943 cm$^{-1}$.

Besides, 3.55 g of the 15β-hydroxy compound is obtained as the polar component (PG numbering).

1(d)
(1R,5S,6R,7R)-7-(Tetrahydropyran-2-yloxy)-6-[(E)-3R-3-(tetrahydropyran-2-yloxy)-4,4-trimethyleneoct-1-en-6-ynyl]bicyclo[3.3.0]octan-3-one A solution of 4.90 of the compound prepared according to Example 1(c) in 150 ml of methanol is agitated overnight with 2.25 g of anhydrous potassium carbonate. The mixture is concentration under vacuum, taken up in 1 liter of ether, shaken with water, and dried over magnesium sulfate. After evaporation of the ether, 4.75 g of a crude diol is obtained which is stirred for 20 hours with 170 ml of a mixture of acetic acid/water-tetrahydrofuran (65/35/10) at room temperature. Subsequently the mixture is evaporated under vacuum and the residue purified by chromatography on silica gel with hexane/ethyl acetate (3 + 7),thus obtaining 2.95 g of the keto diol which is dissolved in 100 ml of dichloromethane and combined at 0° C., with 4 g of dihydropyran and 30 mg of p-toluenesulfonic acid. The mixture is stirred for 30 minutes at 0° C., poured on 50 ml of sodium bicarbonate solution, extracted with dichloromethane, dried over magnesium sulfate, and evaporated under vacuum. The residue is chromatographed on silica gel with hexane/ethyl acetate (7 + 3), thus producing 3.92 g of the title compound as a colorless oil.

IR: 2941, 2868, 1738, 972 cm$^{-1}$.

EXAMPLE 2

(5E)-13,14-Diehydro-18,18,19,19-tetradehydro-16,16trimethylene-6a-carbaprostaglandin I$_2$ At 5° C., 4.75 g of potassium tert-butylate is added within 45 minutes to a solution of 9.40 g of 4-carboxybutyltriphenylphosphonium bromide in 20 ml of dimethyl sulfoxide and 8 ml of tetrahydrofuran; the mixture is agitated for another 45 minutes at 5° C. To the red ylene solution is added a solution of 1.95 g of (1R,5S,6R,7R)-7-(tetrahydropyran-2-yloxy)-6-[(3S)-2-bromo-3-(tetrahydropryan-2-yloxy)-4,4-trimethylenecot-1en-6-ynyl]bicyclo[3.3.0]octan-3-one in 4 ml of tetrahydrofuran and the mixture is stirred for 4 hours at 40° C. Then the mixture is poured on ice water, acidified with citric acid to pH 4, and extracted with dichloromethane, the extract washed with brine, dried over magnesium sulfate, and evaporated under vacuum. The residue is purified by chromatography on silica gal. With hexane/ethyl acetate (3 + 2), 200 mg of the 5Z-configured olefin is first of obtained, and then, as the more polar component, 730 mg of (5E)-13,14-diehydro-18,18,19,19-tetradehydro-16,16-trimethylene-6a-carbaprostaglandin I$_2$ 11,15-bis(tetrahydropyranyl ether) is produced as a colorless oil.

IR: 3520, 2941, 2860, 1710, 1020 cm$^{-1}$.

In order to split off the blocking groups, 700 mg of the product as produced above is stirred with 25 ml of a mixture of acetic acid/water/tetrahydrofuran (65/35/10) overnight at 25° C., evaporated under vacuum, and the residue chromatographed on silica gel with ethyl acetate/0.1% acetic acid, thus obtaining 350 mg of the title compound as a colorless oil.

IR: 3600, 3405 (broad), 2930, 2221, 1711, 1603, 1012 cm$^{-1}$.

The starting material for the above title compound is prepared as follows:

2(a)
(1R,5S,6R,7R)-3,3-Ethylenedioxy-7-benzoyloxy-6-2bromo-3-oxo-4,4-trimethyleneoct-1-en-6-ynyl]bicyclo[3.3.0]octane At 0° C., a solution of 11.8 of 2-oxo-3,3-trimethylenehept-5-ynephosphonic acid dimethyl ester in 75 ml of dimethoxyane is added dropwise to a suspension of 1.81 g of sodium hydride (55% strength in mineral oil) in 180 ml of dimethoxyethane; the mixture is stirred for one hour at 0° C. and then 7.40 g of finely pulverized N-bromo-succinimide is added thereto. The mixture is stirred for 30 minutes at 0° C., combined with a solution of 11.40 g of (1R,5S,6R,7R)-3,3-ethylenedioxy-7-benzoyloxy-6-formylbicyclo[3.3.0]octane in 90 ml of dimethoxyethane, and agitated for 2 hours at 0° C. The mixture is then poured on saturated ammonium chloride solution and extracted with ether. The extract is washed neutral with brine, dried over magnesium sulfate, and evaporated under vacuum. Chromatography of the residue on silica gel with hexane/ ether (1+1) yields 8.92 g of the title compound as an oil.

IR: 2935, 2878, 1712, 1690, 1602, 1588, 1450, 1275, 944 cm$^{-1}$.

2(b)
(1R,5S,6R,7R)-7-Hydroxy-6-[(3S)-2-bromo-3-hydroxy-4,4-trimethyleneoct-1-en-6-ynyl]bicyclo[3.3.0]octan-3-one At $-40°$ C., 3.60 g of sodium borohydride is added in incremental portions to a solution of 8.50 g of the ketone prepared according to Example 2(a) in 175 ml of methanol, and the mixture is stirred for 30 minutes at $-40°$ C. Then the mixture is diluted with ether, washed neutral with brine, dried over magnesium sulfate, and evaporated under vacuum. The crude product (mixture of epimers) is dissolved in 250 ml of methanol, 3.60 g of potassium carbonate is added, and the mixture stirred overnight at 25° C. Subsequently, the mixture is concentrated under vacuum, diluted with ether and washed neutral with brine, dried over magnesium sulfate, and evaporated under vacuum. The residue is stirred for 16 hours at 25° C. with 300 ml of a mixture of acetic acid/water/tetrahydrofuran (65/35/10) and then evaporated under vacuum. Chromatography on silica gel with ether/dichloromethane yields 2.10 g of the 15$\beta$-hydroxy compound (PG numbering), as well as 2.90 g of the title compound (15$\alpha$-hydroxy) as the more polar component in the form of a colorless oil.

IR: 3600, 3420 (broad), 2957, 2931, 1738, 1600, 1405 cm$^{-1}$.

2(c)
(1R,5S,6R,7R)-7-Tetrahydropyran-2-yloxy)-6-[(3S)-2-bromo-3-(tetrahydropyran-2-yloxy)-4,4-trimethyleneoct-1-en-6-ynyl]bicyclo[3.3.0]octan-3-one A solution of 2 g of the $\alpha$-alcohol prepared according to Example 2(b), 20 mg of p-toluenesulfonic acid, and 2 g of dihydropyran in 50 ml of dichloromethane is agitated for 30 minutes at 0° C. Then the mixture is diluted with dichloromethane, shaken with sodium bicarbonate solution and brine, dried over magnesium sulfate, and evaporated under vacuum. After chromatography of the residue on silica gel, hexane/ether (6+4) yields 2.60 g of the title compound as a colorless oil.

IR: 2938, 2865, 1735, 1452, 1121 cm$^{-1}$.

EXAMPLE 3

(5E)-20-Methyl-18,18,19,19-tetrahydro-16,16-trimethylene-6a-carbaprostaglandin I$_2$ Analogously to Example 1, 1.50 g of (1R,5S,6R,7R)-7-tetrahydropyran-2-yloxy)-6-[(E)-(3R)-3-(tetrahydropyran-2-yloxy)-4,4-trimethyleneon-1-en-6-ynyl]bicyclo[3.3.0]octan-3-one yields 630 mg of (5E)-20-methyl-18,18,19,19-tetrahydro-16,16-trimethylene-6a-carbaprostaglandin I$_2$ 11,15-bis(tetrahydropyranyl ether) as a colorless oil.

IR: 3520, 2940, 2862, 1712, 1070, 1020, 974 cm$^{-1}$.

After splitting off the blocking groups according to Example 1, 310 mg of the title compound is obtained as a colorless oil.

IR: 3600, 3520, 3405 (broad), 2938, 2862, 1710, 972 cm$^{-1}$.

The starting materials for the above title compound are produced as set forth below:

3(a) 2-Oxo-3,3-trimethyleneoct-5-ynephosphonic Acid Dimethyl Ester

In analogy to Example 1 (a), 2,2-trimethylene-hept-4-ynoic acid (bp$_{15}$159° C.-160° C.) is obtained from cyclobutanecarboxylic acid and 1-bromo-2-pentyne; esterification yields the methyl ester (bp$_{15}$111° C.-112° C.). Reaction with the lithium compound of the methanephosphonic acid dimethyl ester according to Example 1(a) leads to the title compound, bp 145° C.-147° C. at 0.3 torr.

IR: 3420 (broad), 2982, 2948, 2851, 1702, 1250, 1028 cm$^{-1}$.

3(b)
(1R,5S,6R,7R)-3,3-ethylenedioxy-7-benzoyloxy-6[-(E)-(3-oxo-4,4-trimethylenenon-1-en-6-ynyl]-bicyclo[3.3.0]octane analogously to Example 1 (b), 11.40 g of (1R,5S,6R,7R)-3,3-ethylenedioxy-7-benzoyloxy-6formyl-bicyclo[3.3.0]octane produces, with 2-oxo-3,3trimethylene-oct-5-ynephosphonic acid dimethyl ester 10.02 g of the title compound, as a colorless oil.

IR: 2942, 2861, 1712, 1688, 1620, 1600, 1585, 1270, 981, 944 cm$^{-1}$.

3(c)
(1R,5S,6R,7R)-3,3-ethylenedioxy-7-benzoyloxy-6[-(E)-(3R)-3-hydroxy-4,4-trimethylenenon-1-en-6-ynyl]-bicyclo[3.3.0]octane In analogy to Example 1 (c), 10 g of the compound prepared according to Example 3(b) yields 5.95 g of the title compound, as a colorless oil.

IR: 3600, 3520, 2937, 2880, 1712, 1601, 1585, 1270, 972, 948 cm$^{-1}$.

3(d)
(1R,5S,6R,7R)-7-tetrahydropyran-2-yloxy)-6[-(E)-(3R)-3-(tetrahydropyran-2-yloxy)-4,4-trimethylenenon-1-en-6-ynyl]-bicyclo[3.3.0]octan-3-one Analogously to Example 1 (d), 4.25 g of the title compound is obtained as a colorless oil from 5.50 g of compound prepared according to Example 3(c) by ester cleavage, ketal cleavage, and blockage of the hydroxy groups as the bis(tetrahydropyranyl) ether.

IR: 2940, 2865, 1738, 976 cm$^{-1}$.

EXAMPLE 4

(5E)-20-Ethyl-18,18,19,19-tetrahydro-16,16-trimethylene-6a-carbaprostaglandin I$_2$ In analogy to Example 1, 700 mg of (1R,5S,6R,7R)-7-tetrahydropyran-2-yloxy)-6-[(E)-(3R)-3-(tetrahydropyran-2-yloxy)-4,4-trimethylenedec-1-en-6-ynyl]bicyclo[3.3.0]octan-3-one yields 270 mg of (5E)-20-ethyl-18,18,19,19-tetrahydro-16,16-trimethylene-6a-carbaprostaglandin I$_2$ 11,15-bis(tetrahydropyranyl ether) as a colorless oil.

IR: 3520, 2945, 2870, 1711, 1072, 1020, 976 cm$^{-1}$.

After the blocking groups have been split of according to Example 1, 140 mg of the title compound is obtained as a colorless oil.

IR: 3600, 3505, 3410 (broad), 2940, 1711, 976 cm$^{-1}$.

The starting materials for the above title compound are prepared as follows:

4(a) 2-Oxo-3,3-trimethylenenon-5-ynephosphonic Acid Dimethyl Ester

In analogy to Example 1 (a), cyclobutanoic acid and 1-bromo-2-hexane yield 2,2trimethyleneoct-4-ynoic acid (bp 178° C.–180° C. at 14 torr), which later yields the methyl ester (bp 128° C.–130° C. at 15 torr) after esterification. Reaction with the lithium compound of methanephosphonic acid dimethyl ester according to Example 1(a) leads to the title compound, (bp 150° C.–152° C. at 0.1 torr).

IR: 3420 (broad), 2986, 2951, 2850, 1704, 1250, 1031 cm$^{-1}$.

4(b) (1R,5S,6R,7R)-3,3-Ethylenedioxy-7-benzoyloxy-6-[(E)-3-oxo-4,4-trimethylenedec-1-en-6-ynyl]bicyclo[3.3.0]octane Analogously to Example 1(b), 10.0 g of (1R,5S,6R,7R)-3,3-ethylenedioxy-7-benzoyloxy-6-formyl-]bicyclo[3.3.0]octane, with 2-oxo-3,3-trimethylene-non-5-yne-phosphonic acid dimethyl ester, yields 8.50 g of the title compound as a colorless oil.

IR: 2945, 2860, 1712, 1687, 1601, 1585, 1269, 978, 948 cm$^{-1}$.

4(c) (1R,5S,6R,7R)-3,3-Ethylenedioxy-7-benzoyloxy-6-[(E)-(3R)-3-hydroxy-4,4-trimethylene-dec-1-en-6-ynyl]bicyclo[3.3.0]octane Analogously to Example 1(c), 8.00 g of the compound produced according to Example 4(b) yields 4.85 g of the title compound as a colorless oil.

IR: 3600, 3510, 2940, 2881, 1712, 1600, 1585, 1272, 974, 946 cm$^{-1}$.

4(d) (1R,5S,6R,7R)-7-Tetrahydropyran-2-yloxy)-6-[(E)-(3R)-(3)-(tetrahydropyran-2-yloxy)-4,4-trimethylene-dec-1-en-6-ynyl]bicyclo[3.3.0]octan-3-one In analogy to Example 1(d), 4.00 g of the compound prepared according to Example 3(c) yields, by ester cleavage, ketal cleavage, and blockage of the hydroxy groups as the bis(tetrahydropyranyl) ether, 3.10 g of the title compound as a colorless oil.

IR: 2940, 2860, 1738, 974 cm$^{-1}$.

EXAMPLE 5

(5E)-13,14-Didehydro-20-methyl-18,18,19,19-tetrahydro-16,16-trimethylene-6a-carbaprostaglandin I$_2$ At 5° C., 2.38 g of potassium tert-butylate is added within 45 minutes to a solution of 4.71 g of 4-carboxybutyltriphenylphosphonium bromide in 10 ml of dimethyl sulfoxide and 5 ml of tetrahydrofuran, and the mixture is stirred for 45 minutes at 5° C. To the red ylene solution is added dropwise a solution of 1.00 g of (1R,5S,6R,7R)-7-(tetrahydropyran-2-yloxy)-6-[(3S)-2-bromo-3-(tetrahydropyran-2-yloxy)-4,4-trimethylene-non-1-en-6-ynyl]bicyclo[3.3.0]octan-3-one in 2 ml of tetrahydrofuran, and the mixture is stirred for 4 hours at 40° C., then poured on ice water, acidified with citric acid to pH 4, extracted with dichloromethane, and the extract is washed with brine, dried over magnesium sulfate, and evaporated under vacuum. The residue is purified by chromatography on silica gel. With hexane/ethyl acetate (1+1), 170 mg of (5Z)-13,14-didehydro-20-methyl-18,18,19,19-tetrahydro-16,16-trimethylene-6a-carbaprostaglandin I$_2$ 11,15-bis(tetrahydropyranyl ether) is obtained first of all, and 430 mg of the corresponding 5E-compound is then obtained as the more polar component; this latter compound is stirred for 16 hours at 25° C. with 15 ml of a mixture of acetic acid/water/tetrahydrofuran (65/35/10) to split off the blocking groups, evaporated, and the residue purified by chromatography on silica gel with ethyl acetate, thus obtaining 190 g of the title compound as a colorless oil.

IR: 3600, 3410 (broad), 2935, 1712, 1602, 1015 cm$^{-1}$.

The starting material for the above title compound is prepared as follows:

5(a) (1R,5S,6R,7R)-3,3-Ethylenedioxy-7-benzoyloxy-6-(2-bromo-3-oxo-4,4-trimethylenenon-1-en-6-ynyl]bicyclo[3.3.0]octane Analogously to Example 2(a), 6.49 g of 2-oxo-3,3-trimethyleneoct-5-ynephosphonic acid dimethyl ester, 3.70 of N-bromosuccinimide, and 5.70 g of (1R,5S,6R,7R)-3,3-ethylenedioxy-7-benzoyloxy-6-formylbicyclo[3.3.0]octane, yield 5.10 g of the title compound as an oil.

IR: 2942, 2877, 1712, 1688, 1600, 1585, 1451, 1270, 948 cm$^{-1}$.

5(b) (1R,5S,6R,7R)-7-Hydroxy-6-[3S)-2-bromo-3-hydroxy-4,4-trimethylenenon-1-en-6-ynyl]bicyclo[3.3.0]octan-3-one Analogously to Example 2(b), 5 g of the compound obtained according to Example 5(a) yields, by reduction with sodium borohydride, splitting off the benzoate with potassium carbonate in methanol, and ketal splitting, 1.75 g of the title compound as a colorless oil.

IR: 3600, 3410 (broad), 2955, 2930, 1738, 1600, 1407 cm$^{-1}$.

5(c) (1R,5S,6R,7R)-7-Tetrahydropyran-2-yloxy)-6-[(3S)-2-bromo-3(tetrahydropyran-2-yloxy)4,4-trimethylenenon-1-en-6-ynyl]bicyclo[3.3.0]octan-3-one Analogously to Example 2(c), 1.50 g of the diol prepared according to Example 5(b) yields, with dihydropyran and p-toluenesulfonic acid, 1.95 g of the title compound as a colorless oil.

IR: 2940, 2861, 1738, 1450, 1120 cm$^{-1}$.

EXAMPLE 6

(5Z)-13,14-Didehydro-20-methyl-18,18,19,19-tetrahydro-16,16-trimethylene-6a-carbaprostaglandin I$_2$ At 25° C., 160 mg of (5Z)-13,14-didehydro-20-methyl-18,18,19,19-tetrahydro-16,16-trimethylene-6a-carbaprostaglandin I$_2$ 11,15-bis(tetrahydropyranyl ether) (prepared according to Example 5) is stirred for 16 hours with 5 ml of a mixture of acetic acid/water/tetrahydrofuran (65/35/10). The mixture is then evaporated under vacuum and the residue purified by chromatography on silica gel with ethyl acetate, thus obtaining 75 mg of the title compound as a colorless oil.

IR: 3600, 3410 (broad), 2938, 2221, 1712, 1600, 1015 cm⁻¹.

EXAMPLE 7

(5E)-20-Ethyl-13,14-didehydro-18,18,19,19-tetrahydro-16,16-trimethylene-6a-carbaprostaglandin I₂

Analogously to Example 2, 1.50 g of (1R,5S,6R,7R)-7-tetrahydropyran-2-yloxy)-6-[(3S)-2-bromo-3(tetrahydropyran-2-yloxy)4,4-trimethylenedec-1-en-6-ynyl]-bicyclo[3.3.0]octan-3-one yields 270 mg of a the title compound as a colorless oil.

IR: 3600, 3410 (broad), 2932, 2226, 1712, 1601, 1015 cm⁻¹.

The starting material for the above title compound is prepared as follows:

7(a)

(1R,5S,6R,7R)-3,3-Ethylenedioxy-7-benzoyloxy-6-(2-bromo-3-oxo-4,4-trimethylenedec-1-en-6-ynyl]bicyclo[3.3.0]octane In analogy to Example 2(a), 11.25 g of the title compound is obtained as an oil from 12.9 g of 2-oxo-3,3-trimethylenenon-5-ynephosphonic acid dimethyl ester, 7.40 g of N-bromosuccinimide, and 11.40 g of (1R,5S,6R,7R)-3,3-ethylenedioxy-7-benzoyloxy-6-formylbicyclo[3.3.0]octane.

IR: 2941, 2875, 1711, 1690, 1602, 1586, 1451, 1275, 948 cm⁻¹.

7(b)

(1R,5S,6R,7R)-7-Hydroxy-6-[3S)-2-bromo-3-hydroxy-4,4-trimethylenedec-1-en-6-ynyl]bicyclo[3.3.0]octan-3-one Analogously to Example 2(b), 10 g of the ketone prepared according to Example 7(a) yields 2.52 g of the title compound as a colorless oil.

IR: 3600, 3420 (broad), 2955, 2930, 1738, 1600, 1402 cm⁻¹.

7(c)

(1R,5S,6R,7R)-7-Tetrahydropyran-2-yloxy)-6-[(3S)-2-bromo-3-(tetrahydropyran-2-yloxy)4,4-trimethylenedoc-1-en-6-ynyl]bicyclo[3.3.0]octan-3-one Analogously to Example 2(c), 2 g of the diol prepared according to Example 7(b) yields 2.45 g of the title compound as a colorless oil.

IR: 2942, 2862, 1737, 1453, 1120 cm⁻¹.

EXAMPLE 8

(5E)-20-Methyl-18,18,19,19-tetrahydro-16,16-trimethylene-6a-carbaprostaglandin I₂

Analogously to Example 1, 1.50 g of (1R,5S,6R,7R)-7-(tetrahydropyran-2-yloxy)-6-[(3S)-3-(tetrahydropyran-2-yloxy)4,4-trimethylenedec-1-en-7-ynyl]bicyclo[3.3.0]octan-3-one yields 300 mg of a the title compound as a colorless oil.

IR: 3600, 3405 (broad), 2938, 2855, 1711, 976 cm⁻¹.

8(a) 2-Oxo-3,3-trimethyleneoct-6-ynephosphonic Acid Dimethyl Ester

The process of Example 1(a) is analogously conducted first of all, thus obtaining, from cyclobutanecarboxylic acid and 1-bromo-3-pentyne, 2,2-trimethylene-hept-5-ynoic acid (bp 155° C.–158° C. at 14 torr); by esterification with methanol/sulfuric acid, the 2,2-trimethylene-hept-5-ynoic acid methyl ester is produced (bp 108° C.–110° C. at 15 torr).

IR: 2965, 2950, 2921, 2849, 1728, 1430, 1330, 1097, 970, 870 cm⁻¹.

From this product, with methanephosphonic acid dimethyl ester, the title compound is obtained according to Example 1(a) as a colorless liquid, bp 148° C.–150° C. at 0.3 torr.

IR: 3420 (broad), 2990, 2954, 2848, 1702, 1250, 1030 cm⁻¹.

8(b)

(1R,5S,6R,7R)-3,3-Ethylenedioxy-7-benzoyloxy-6-[(E)-3-oxo-4,4-trimethylenenon-1-en-7-ynyl]bicyclo[3.3.0]octane In analogy to Example 1(a), 11.30 g of the title compound is obtained as a colorless oil from 10 g of (1R,5S,6R,7R)-3,3-ethylenedioxy-7-benzoyloxy-6-formyl-]bicyclo[3.3.0]octane and the phosphonate produced in accordance with Example 8(a).

IR: 2942, 2860, 1710, 1688, 1620, 1600, 1585, 1275, 980, 948 cm⁻¹.

8(c)

(1R,5S,6R,7R)-3,3-Ethylenedioxy-7-benzoyloxy-6-[(E)-(3R)-3-hydroxy-4,4-trimethylene-1-en-7-ynyl]bicyclo[3.3.0]octane Analogously to Example 1(c), 11.0 g of the ketone prepared according to Example 8(b) yields 7.51 g of the title compound (15α-hydroxy) as a colorless oil.

IR: 3600, 3510, 2940, 2881, 1712, 1600, 1585, 1275, 974, 947 cm⁻¹.

8(d)

(1R,5S,6R,7R)-7-Tetrahydropyran-2-yloxy)-6-[(E)-(3R)-(3)-(tetrahydropyran-2-yloxy)-4,4-trimethylene-non-1-en-7-ynyl]bicyclo[3.3.0]octan-3-one In analogy to Example 1(d), 5 g of the 15α-alcohol prepared according to Example 8(c) produces 4.05 g of the title compound as a colorless oil.

IR: 2940, 2862, 1738, 974 cm⁻¹.

EXAMPLE 9

(5E)-13,14-Didehydro-20-methyl-18,18,19,19-tetrahydro-16,16-trimethylene-6a-carbaprostaglandin I₂

Analogously to Example 2, 105 mg of the title compound is obtained as a colorless oil from 500 mg of (1R,5S,6R,7R)-7-(tetrahydropyran-2-yloxy)-6-[(3S)-2-bromo-3-(tetrahydropyran-2-yloxy)-4,4-trimethylene-non-1-en-7-ynyl]bicyclo[3.3.0]octan-3-one.

IR: 3600, 3410 (broad), 2938, 2228, 1710, 1601, 1010 cm⁻¹.

9(a)

(1R,5S,6R,7R)-3,3-Ethylenedioxy-7-benzoyloxy-6-(2-3-oxo-4,4-trimethylenenon-1-en-7-ynyl]bicyclo[3.3.0]octane In analogy to Example 2(a), 5 g of (1R,5S,6R,7R)-3,3-ethylenedioxy-7-benzoyloxy-6-formyl-]bicyclo[3.3.0]octane produces, with 2-oxo-3,3-trimethylene-oct-6-ynephosphonic acid dimethyl ester and N-bromosuccinimide, 4.75 g of the title compound as a colorless oil.

IR: 2938, 2876, 1712, 1688, 1602, 1588, 1451, 1270, 948, cm⁻¹.

9(b)
(1R,5S,6R,7R)-7-Hydroxy-6-[3S)-2-bromo-3-hydroxy-4,4-trimethyleneon-1-en-7-ynyl]bicyclo[3.3.0]octan-3-one In analogy to Example 2(b), 3.10 g of the ketone prepared according to Example 9(a) yields 700 mg of the title compound (15α-hydroxy) as a colorless oil.

IR: 3600, 3410 (broad), 2955, 2930, 1738, 1600, cm$^{-1}$.

9(c)
(1R,5S,6R,7R)-7-Tetrahydropyran-2-yloxy)-6-[(3S)-2-bromo-3(tetrahydropyran-2-yloxy)4,4-trimethylenenon-1-en-7-ynyl]bicyclo[3.3.0]octan-3-one Analogously to Example 2(c), 600 g of the diol prepared according to Example 9(b) yields 730 g of the title compound as a colorless oil.

IR: 2940, 2868, 1740, 1451, 1120 cm$^{-1}$.

EXAMPLE 10
(5E)-18,18,19,19-Tetrahydro-16,16-tetramethylene-6a-carbaprostaglandin I$_2$ In analogy to Example 1, 105 mg of the title compound is obtained as a colorless oil from 500 mg of (1R,5S,6R,7R)-7-tetrahydropyran-2-yloxy)-6-[(E)-(3R)-3-tetrahydropyran-2-yloxy)4,4-trimethyleneoct-1-en-6-ynyl]bicyclo[3.3.0]octan-3-one.

IR: 3600, 3525, 3410 (broad), 2938, 2860, 1710, 976 cm$^{-1}$.

The starting materials for the above title compound are prepared as set forth below:

10(a) 2-Oxo-3,3-trimethylenehept-5-yne-phosphonic Acid Dimethyl Ester

At −30° C., 265 ml of 1.66-molar butylithium solution in hexane is added to a solution of 44.52 g of diisopropylanmine in 200 m of tetrahydrofuran. Then 22.83 g of cyclopentanecarboxlic acid is added dropwise to the mixture, the latter is agitated for 30 minutes at −10° C., and then 31.92 g of 1-bromo-2-butyne is added dropwise; the mixture is stirred for 16 hours at 25° C., and poured on 600 ml of ice water, acidified with hydrochloric acid, extracted with ether, the extract is washed with brine, and concentrated under vacuum. After distillation of the residue, 21.30 g of 2,2-trimethylene-hex-4-ynoic acid is obtained, bp 155° C.-157° C. at 13 torr.

IR: 3520 (broad), 2982, 2960, 1702. 1425, 1100, 1035, cm$^{-1}$.

For esterification, 20 g of the acid is refluxed in 250 ml of methanol and 2.5 ml of concentrated sulfuric acid for 6 hours, thus obtaining 18.10 g of 2,2-trimethylene-hex-4-ynoic acid methyl ester, bp 110° C.-111° C. at 14 torr.

IR: 2951, 2860, 1728, 1430, 1331, 1098 cm$^{-1}$.

This ester is converted into the title compound according to Example 1(a) by reaction with 2,2-trimethylenehept-5-ynephosphonic acid dimethyl ester; bp 120° C.-122° C. at 0.16 torr.

IR: 3425 (broad), 2980, 2951, 2853, 1705, 1250, 1033 cm$^{-1}$.

10(b)
(1R,5S,6R,7R)-3,3-Ethylenedioxy-7-benzoyloxy-6-[(E)-3-oxo-4,4-trimethyleneoct-1-en-6-ynyl]bicyclo[3.3.0]octane Analogously to Example 1(b), 5 g of (1R,5S,6R,7R)-3,3-ethylenedioxy-6-formylbicyclo[3.3.0]octane, yields with 2-oxo-3,3-trimethylenehept-5-ynephosphonic acid dimethyl ester, 5.35 g of the title compound as a colorless oil.

IR: 2940, 2865, 1711, 1684, 1622, 1600, 1585, 1275, 978, 947 cm$^{-1}$.

10(c)
(1R,5S,6R,7R)-3,3-Ethylenedioxy-7-benzoyloxy-6-[(E)-(3R)-3-hydroxy-4,4-trimethyleneoct-1-en-6-ynyl]bicyclo[3.3.0]octane In analogy to Example 1(c), 5.20 g of the ketone produced according to Example 10(b) yields 2.95 g of the title compound as a colorless oil.

IR: 3600, 3515, 2945, 2878, 1712, 1601, 1585, 1274, 976, 947 cm$^{-1}$.

10(d)
(1R,5S,6R,7R)-7-Tetrahydropyran-2-yloxy)-6-[(E)-(3R)-(3)-(tetrahydropyran-2-yloxy)-4,4-trimethylenedoct-1-en-6-ynyl]bicyclo[3.3.0]octan-3-one Analogously to Example 1(d), 2.75 g of the compound prepared according to Example 10(c) yields 2.05 g of the title compound as a colorless oil.

IR: 2943, 2870, 1740, 976 cm$^{-1}$.

EXAMPLE 11
(5E)-18,19-Didehydro-19-methyl-16,16-tetrahydro-6a-carbaprostaglandin I$_2$ In analogy to Example 1, 112 mg of the title compound is obtained as a colorless oil from 500 mg of (1R,5S,6R,7R)-7-(tetrahydropyran-2-yloxy)-6-[(E)-(3R)-7-methyl-3-(tetrahydropyran-2-yloxy)-4,4-trimethylenenoct-1,6-dienyl]bicyclo[3.3.0]octan-3-one.

IR: 3600, 3520, 3410 (broad), 2935, 1711, 1601, 976 cm$^{-1}$.

The starting materials for the above title compound are produced as follows:

11(a) 6-Methyl-2-oxo-3,3-trimethylenehept-5-enephosphonic Acid Dimethyl Ester At −30° C., 318 ml of 1.66-molar butylithium solution in hexane is added to a solution of 53.10 g of diisopropylanmine in 250 m of tetrahydrofuran, and thereafter 24.02 g of cyclopentanecarboxlic acid is added thereto. The mixture is stirred for 30 minutes at −10° C. and then 42.91 g of 1-bromo-2-butyne is added dropwise thereto and the mixture is stirred for 18 hours at 25° C. Subsequently the mixture is poured on 1 liter of ice water, adjusted to pH 4 with 2N hydrochloric acid, extracted width ether, the extract is washed with brine, and dried over magnesium sulfate, and the ether is evaporated under vacuum. The residue is distilled, thus obtaining 26.30 g of 5-methyl-2,2-trimethylene-hex-4-enoic acid (bp 158° C.-159° C. at 14 torr), yielding analogously to Example 1(a) 23.5 g of 5-methyl-2,2-trimethylenehex-4-enoic acidmethyl ester (bp 108° C.-110° C. at 14 torr).

IR: 2980, 2948, 2857, 1728, 1430, 1080, 932, cm$^{-1}$.

From 20 g of the methyl ester produced above, 23.30 g of the title compound is obtained as a colorless liquid, bp 138° C.-140° C. at 15 torr, by reaction with methanephosphonic acid dimethyl ester in accordance with Example 1(a).

IR: 3420 (broad), 2988, 2950, 2855, 1704, 1250, 1035 cm$^{-1}$.

11(b)
(1R,5S,6R,7R)-3,3-Ethylenedioxy-7-benzoyloxy-6-[(E)-7-methyl-3-oxo-4,4-trimethyleneocta-1,6-dienyl]bicyclo[3.3.0]octane In analogy to Example 1(b), 5 g of (1R,5S,6R,7R)-3,3-ethylenedioxy-6-formylbicyclo[3.3.0]octane and the phosphate produced according to Example 11(a) yield 5.95 g of the title compound as a colorless oil.

IR: 2948, 2860, 1712, 1620, 1600, 1585, 1272, 977, 948 cm$^{-1}$.

11(c)
(1R,5S,6R,7R)-3,3-Ethylenedioxy-7-benzoyloxy-6-[(E)-(3R)-3-hydroxy-7-methyl-4,4-trimethyleneocta-1,6-dienyl]bicyclo[3.3.0]octane In analogy to Example 1(c), 2.88 g of the title compound (15α-hydroxy) is obtained as a colorless oil from 5.00 g of the ketone prepared according to Example 11(b).

IR: 3600, 3510, 2940, 2868, 1712, 1600, 1584, 1272, 978, 948 cm$^{-1}$.

11(d)
(1R,5S,6R,7R)-7-Tetrahydropyran-2-yloxy)-6-[(E)-(3R)-7-methyl-3-(tetrahydropyran-2-yloxy)-4,4-trimethyleneocta-1,6-dienyl]bicyclo[3.3.0]octan-3-one In analogy to Example 1(d), 2.50 g of the compound prepared according to Example 11(c) yields 1.90 g of the title compound as a colorless oil.

IR: 2940, 2871, 1738, 976 cm$^{-1}$.

EXAMPLE 12
(5E)-18,18,19,19-Tetrahydro-16,16-trimethylene-N-methanesulfonyl-6a-carbaprostaglandin $I_2$ Carboxamide At 0° C., a solution of 190 mg of (5E)-18,18,19,19-tetrahydro-16,16-trimethylene-6a-carbaprostaglandin $I_2$ (prepared according to Example 1) in 4 ml of dimethylformamide is combined with 80 mg of chloroformic acid butyl ester and 60 mg of trietylaine. After 30 minutes, 240 mg of the sodium salt of methylsulfonamide (prepared from methylsulfonamide and sodium methylae) and 1 ml of hexamethylphosphoric triamide are added to the mixture and the latter is stirred for 3 hours at 25° C. Subsequently the reaction mixture is poured in citrate buffer (pH 5), repeatedly extracted with ethyl acetate, the organic phase is washed with brine, dried over magnesium sulfate, and evaporated under vacuum. Chromatography of the residue on silica gel with dichloromethane and 1%-5% isopropanol yields 135 mg of the title compound as a colorless oil.

IR: 3600, 3410 (broad), 2960, 2855, 1728, 976 cm$^{-1}$.

EXAMPLE 13
(5E)-13,14-Didehydro-18,18,19,19-tetrahydro-16,16-trimethylene-6a-carbaprostaglandin $I_2$ Carboxamide 200 mg of (5E)-13,13-didehydro-18,18,19,19-tetrahydro-16,16-trimethylene-6a-carbaprostaglandin $I_2$ (See Example 2) is dissolved in 5 ml of tetrahydrofuran and combined at 0° C. with 90 mg triethylamine and 98 mg of chloroformic acid isobutyl ester. After 1 hour, gaseous ammonia is introduced at 0° C. for 10 minutes, whereafter the reaction mixture is left for one hour at 25° C. then diluted with water, extracted with dichloromethane, the extract is washed with brine, dried over magnesium sulfate, and evaporated under vacuum. Purification by chromatography on silica gel with chloroform/1%-5% isopropanol yields 160 mg of the title compound as a colorless oil.

IR: 3600, 3540, 3405, 2955, 2868, 2220, 1670, 1588 cm$^{-1}$.

EXAMPLE 15
(5E)-18,19-Didehydro-19-chloro-16,16-trimethylene-6a-carbaprostaglandin $I_2$ Analogously to Example 1, 2 g of (1R,5S,6R,7R)-7-(tetrahydropyran-2-yloxy)-6-[(E)-(3R)-7-chloro-3-(tetrahydropyran-2-yloxy)-4,4-trimethylenenocta-1,6-dienyl]bicyclo[3.3.0]octan-3-one yields, by a Wittig reaction (6 hours at room temperature) and subsequent cleavage of blocking groups, 130 mg of the title compound as a colorless oil.

IR (Film): 3500 (broad), 2930, 2850, 1710, 1660, 975 cm$^{-1}$.

The starting materials for the above title compound are produced as follows:

14(a)
6-Chloro-2-oxo-3,3-trimethylenehept-5-ene-phosphonic Acid Dimethyl Ester At −30° C., 267 ml of 1.66-molar butylithium solution in hexane is added to a solution of 45 g of diisopropylanmine in 200 m of tetrahydrofuran; then 20.2 g of cyclopentanecarboxlic acid is added thereto. After 30 minutes of agitation at −10° C., 30 g of 1,3-dichloro-2-butene is added dropwise to the reaction mixture. The latter is agitated for 16 hours at room temperature, then poured on 1 liter of ice water, adjusted to pH 4 with 2N hydrochloric acid, extracted width ether, the combined organic phases are washed with saturated sodium chloride solution, dried over magnesium sulfate, and concentrated under vacuum. The residue is purified by distillation, thus obtaining 22.3 g of 5-chloro-2,2-trimethylene-hex-4-enoic acid (bp 146° C.-150° C. at 4 torr); this product, analogously to Example 1(a), yields 21 g of 5-chloro-2,2-trimethylenehex-4-enoic acid methyl ester (bp 107° C.-110° C. at 4 torr).

IR (Film): 2970, 2950, 2890, 1735, 1664, 1195, 1170 cm$^{-1}$.

According to the directions given in Example 1(a), 20.5 g of the title compound is obtained as a colorless liquid from the above 21 g of methyl ester by reaction with methanephosphonic acid dimethyl ester.

IR: 3400, 2980, 2945, 2850, 1710, 1666, 1260, 1030 cm$^{-1}$.

14(b)
(1R,5S,6R,7R)-3,3-Ethylenedioxy-7-benzoyloxy-6-[(E)-7-chloro-3-oxo-4,4-trimethyleneocta-1,6-dienyl]bicyclo[3.3.0]octane In analogy to the directions in Example 1(b), 6 g of (1R,5S,6R,7R)-3,3-ethylenedioxy-6-formylbicyclo[3.3.0]octane and the phosphonate disclosed in Example 14(a) yield 6.2 g of the title compound as a colorless oil.

IR (Film): 2950, 2855, 1720, 1670, 1630, 1600, 1583, 1270, 715 cm$^{-1}$.

14(c)
(1R,5S,6R,7R)-3,3-Ethylenedioxy-7-benzoyloxy-6-[(E)-(3R)-7-chloro-3-hydroxy-4,4-trimethyleneocta-1,6-dienyl]bicyclo[3.3.0]octane In analogy to Example 1(c), 6.2 g of the α,β-unsaturated ketone produced according to Example 14(b) yields 3.2 g of the title compound (15α-alcohol) as a colorless oil.

IR (Film): 3500, (broad), 2950, 2860, 1720, 1665, 1600, 1580, 1270, 715 cm$^{-1}$.

14(d)

(1R,5S,6R,7R)-7-Tetrahydropyran-2-yloxy)-6-[(E)-(3R)-7-chloro-3-(tetrahydropyran-2-yloxy)-4,4-trimethylenedeca-1,6-dienyl]bicyclo[3.3.0]octan-3-one Analogously to the directions given in Example 1(d), 3.1 g of the compound prepared according to Example 14(c) yields 2.3 g of the title compound as a colorless oil.

IR (Film): 2940, 2870, 1735, 1665, 1180, 1125, 1080, 1020 cm$^{-1}$.

EXAMPLE 15

(5E)-3-Oxa-18,19-tetradehydro-16,16-tetramethylene-6a-carbaprostaglandin $I_2$ 113 mg of 55% strength sodium hydride suspension (in mineral oil) is added to a solution of 510 mg of 2-[(E)-(1S,5S,6R,7R)-7-(tetrahydropyran-2-yloxy)-6-[(E)-(3R)-3-(tetrahydropyran-2-yloxy)-4,4-trimethylenoct-1-en-6-ynyl]bicyclo[3.3.0]octan-3-ylidene]ethan-1-ol in 15 ml of tetrahydrofuran; the mixture is boiled under reflex for one hour. Then a solution of 166 mg of bromoacetic acid in 5 ml of tetrahydrofuran is added to the reaction mixture; the latter is refluxed for 18 hours, diluted with ether, and shaken four times with respectively 25 ml of 4% sodium hydroxide solution. This extract is adjusted to pH 3 with 10% strength sulfuric acid at 0° C., and extracted with methylene chloride. The organic extract is shaken with brine, dried over magnesium sulfate, and evaporated under vacuum, thus producing 440 mg of (5E)-3-oxa-18,19-tetradehydro-16,16-tetramethylene-6a-carbaprostaglandin $I_2$ 11, 15-bis-(tetrahydropyranyl ether) which is stirred, to split off the blocking groups, for 18 hours with 30 ml of acetic acid/water/ tetrahydrofuran at 25° C. The mixture is evaporated with the addition of toluene and the residue is chromatographed on silica gel with ethyl acetate/0.1%-1% acetic acid, thus obtaining 283 mg of the title compound as a colorless acid.

IR (CHCl$_3$): 3680, 3400 (broad), 2930, 1730, 1600, 1425, 970 cm$^{-1}$.

The starting materials for the above title compound is prepared as set out below:

15(a)

(2-[(E)-1S,5S,6R,7R)-7-Tetrahydropyran-2-yloxy)-6-[(E)-(3R)-3-tetrahydropyran-2-yloxy)4,4-trimethyleneoct-1en-6-ynyl]-bicyclo[3.3.0]octan-3-ylidene]ethan-1-ol At 0° C., 1.42 g of potassium tert-butylate is added to a solution of 3.32 g of phosphonoacetic acid triethyl ester in 75 ml of tetrahydrofuran; the mixture is stirred for 10 minutes, combined with a solution of 4 g of (1R,5S,6R,7R)-7-(tetrahydropyran-2-yloxy)-6-[(E)-(3R)-3-tetrahydropyran-2-yloxy)4,4-trimethyleneoct-1en-6-ynyl]-bicyclo[3.3.0]octan-3-one in 40 ml of toluene, and agitated for 18 hours at 24° C. The mixture is then diluted with 400 ml of ether, shaken once with water, once with 20% sodium hydroxide solution, washed neutral with water, dried over magnesium sulfate, and evaporated under vacuum. The residue is filtered with hexane/ether (1+1) over silica gel, thus obtaining 4 g of the unsaturated ester as a colorless oil.

IR: 2940, 2870, 1700, 1652, 972 cm$^{-1}$.

At 0° C., 1.1 g of lithium aluminum hydride is added in incremental portions to a stirred solution of 4 g of the above-produced ester in 130 ml of ether, and the mixture is agitated for 30 minutes at 0° C. The excess reagent is destroyed by dropwise addition of ethyl acetate, 6 ml of water is added, the mixture is stirred for 2 hours at 20° C., filtered, and evaporated under vacuum. The residue is chromatographed with ether/hexane (3+2) on silica gel, thus obtaining as the lesser polar compound 1.1 (2-[(Z)-(1S,5S,6R,7R)-7-(tetrahydropyran-2-yloxy)-6-[(E)-(3R)-3-tetrahydropyran-2-yloxy)4,4-trimethylene-oct-1en-6-ynyl]-bicyclo[3.3.0]octan-3-ylidene]ethan-1-ol and 2.1 g of the title compound as colorless oils.

IR: 3600, 3450, 2940, 2865, 1600, 974 cm$^{-1}$.

EXAMPLE 16

(5Z)-3-Oxa-18,18,19,19-tetradehydro-16,16-trimethylene-6a-carbaprostaglandin $I_2$ Analogously to Example 15, 490 mg of 2-[(Z)-(1S,5S,6R,7R),-7-(tetrahydropyran-2-yloxy)-4,4-trimethylene-oct-1-en-6-ynyl]bicyclo[3.3.0]octan-3-ylidene]ethan-1-ol yields 220 mg of the title compound as a colorless oil.

IR: 3600, 3400 (broad), 2930, 1732, 1600, 972 cm$^{-1}$.

EXAMPLE 17

(5E)-13,14-Didehydro-3-oxa-18,18,19,19-tetrahydro-16,16-trimethylene-6a-carbaprostaglandin $I_2$ 60 mg of 55% strength sodium hydride suspension (in mineral oil) is added to a solution of 260 mg of (2-[(E)-(1S,5S,6R,7R)-7-(tetrahydropyran-2-yloxy)-6-[(3S)-3-tetrahydropyran-2-yloxy)4,4-trimethyleneocta-1,6-diynyl]-bicyclo[3.3.0]octan-3-ylidene]ethan-1-ol in 7 ml of tetrahydrofuran, and the mixture is refluxed for one hour. Then a solution of 82 mg of bromoacetic acid in 2.5 ml of tetrahydrofuran is added thereto, the mixture is refluxed for 18 hours, diluted with ether, and extracted four times with respectively 15 ml of 4% sodium hydroxide solution. This extract is adjusted to pH 3 with 10% strength sulfuric acid at 0° C. and with methylene chloride. The organic extract is shaken with brine, dried over magnesium sulfate, and evaporated under vacuum, thus obtaining 250 mg of of (5E)-13,14-didehydro-3-oxa-18,18,19,19-tetrahydro-16,16-trimethyl-6a-carbaprostaglandin $I_2$ 11,15-bis(tetrahydropyranyl ether) which, for splitting off the blocking groups, is stirred for 18 hours at 25° C. with 12 ml of acetic acid/water/tetrahydrofuran. The product is concentrated by evaporation with the addition of toluene and the residue is chromatographed on silica gel with ethyl acetate/0.1%-1% acetic acid, thus obtaining 130 mg of the title compound as a colorless oil.

IR: 3680, 3400 (broad), 2930, 2225, 1730, 1602 cm$^{-1}$.

The starting material for the above title compound is prepared as follows:

17(a)

(1R,5S,6R,7R)-3,3-Ethylenedioxy-7-tetrahydropyran-2-yloxy)-6-([(3S)-2-bromo-3-(tetrahydropyran-2-yloxy)-4,4-trimethyleneoct-1-en-6-ynyl]bicyclo[3.3.0]octane At −40° C., 1.2 g of sodium borohydride is added in incremental portions to a solution of 3 g of (1R,5S,6R,7R)-3,3-ethylenedioxy-7-benzoyloxy-6-(2-bromo-3-oxo-4,4-trimethylenect-1-en-7-enyl)bicyclo[3.3.0]octane in 70 methanol, and the mixture is agitated for 45 minutes at −40° C. Then the mixture is diluted with ether, washed neutral with water, dried over magnesium sulfate, and evaporated under vacuum. The crude product (mixture of 15-epimers) is dissolved in 100 ml of methanol, 1.2 g of potassium carbonate is added, and the mixture is stirred for 20 hours at 23° C. under argon. Subsequently the mixture is concentrated under vacuum, diluted with ether, and washed neutral with brine, then dried over magnesium sulfate, and evaporated under vacuum. Column chromatography on silica gel with ether/hexane (3+2) yields initially 0.8 g of the 15β-configured alcohol, and, as the more polar component, 0.9 g of the 15α-configured compound (PG nomenclature) as a colorless oil.

A solution of 0.8 g of the α-alcohol, 8 mg of p-toluenesulfonic acid, and 0.7 g of dihydropyran in 25 ml of methylene chloride is agitated for 45 minutes at 0° C. Then the mixture is diluted with ether, shaken with dilute sodium bicarbonate solution, washed neutral with water, dried over magnesium sulfate, and evaporated under vacuum. After chromatography of the residue on silica gel, 1.1 g of the title compound is obtained with hexane/ether (7+3) in the form of a colorless oil.

IR: 2940, 2875, 1450, 948 cm$^{-1}$.

17(b)

(1R,5S,6R,7R)-7-tetrahydropyran-2-yloxy)-6-[(3S)-3-tetrahydropyran-2-yloxy)4,4-trimethyleneocta-1,6-diynyl]-bicyclo[3.3.0]octan-3-one A solution of 1.1 g of the compound produced according to Example 17(a) in 12 ml of dimethyl sulfoxide and 5 ml of tetrahydrofuran is combined with 352 mg of potassium tert-butylate, and the mixture is agitated for 2 hours at 22° C., then diluted with 50 ml of water, and extracted three times with respectively 50 ml of ether/hexane (3+2). The extract is washed with water, dried over magnesium sulfate, and evaporated under vacuum. The residue is stirred for 20 hours with 30 ml of acetic acid/water/tetrahydrofuran (65/35/10), evaporated under vacuum, and the remainder chromatographed on silica gel for purification. With ether, 0.6 g of an oily compound is eluted; this compound is reacted in 20 ml of methylene chloride with 0.45 g of dihydropyran and 5 mg of p-toluene-sulfonic acid at 0° C. After 30 minutes, the mixture is diluted with ether, extracted with sodium bicarbonate solution and water, dried over magnesium sulfate, and evaporated under vacuum. Chromatography on silica gel with hexane/ether (1+1) yields 0.8 g of the title compound as a colorless oil.

IR: 2945, 2880, 2210, 1736 cm$^{-1}$.

17(c)

2-[(E)-(1S,5S,6S,7R)-7-tetrahydropyran-2-yloxy)-6-([(3S)-3-(tetrahydropyran-2-yloxy)-4,4-trimethyleneocta-1,6-diynyl]bicyclo[3.3.0]octan-3-ylidene]ethan-1-ol At 0° C., 280 mg of potassium tert-butylate is added to a solution of 0.66 g of phosphonoacetic acid triethylester in 15 ml of tetrahydrofuran; the mixture is stirred for 10 minutes, combined with a solution of 0.8 g of the ketone produced according to Example 17(b) in 8 ml of toluene, and is agitated for 18 hours at 24° C. the mixture is then diluted with 100 ml of ether, shaken once with water, once with 20% sodium hydroxide solution, washed neutral with water, dried over magnesium sulfate, and evaporated under vacuum. The residue is filtered with hexane/ether (1+1) over silica gel thus obtaining 0.81 g of the unsaturated ester as a colorless oil.

IR: 2942, 2873, 2210, 1700, 1650 cm$^{-1}$.

In incremental portions, 220 mg of lithium aluminum hydride is added at 0° C. to an agitated soluiton of 0.8 g of the aforementioned ester in 25 ml of ether, and the mixture is stirred at 0° C. for 30 minutes. Excess reagent is destroyed by dropwise addition of ethyl acetate, 1 ml of water is added, the mixture is stirred for 2 hours at 20° C., filtered and evaporated under vacuum. The residue is chromatographed with ether/hexane (3+2) on silica gel, thus obtaining, as the less polar compound, 230 mg of 2-[(Z)-(1S,5S,6S,7R)-7-(tetrahydropyran-2-yloxy)-6-[(3S)-3-tetrahydropyran-2-yloxy)4,4-trimethyleneocta-1,6-diynyl]-bicyclo[3.3.0]octan-3-ylidene)ethan-1-ol and 240 mg of the title compound as colorless oils.

IR: 3600, 3450, 2940, 2215 cm$^{-1}$.

EXAMPLE 18

(5E)-3-Oxa-20-methyl-18,18,19,19-tetrahydro-16,16-trimethylene-6a-carbaprostaglandin I$_2$ Analogously to Example 15, 300 mg of (2-[(E)-(1S,5S,6R,7R)-7-(tetrahydropyran-2-yloxy)-6-[(E)-(3R)-3-tetrahydropyran-2-yloxy)4,4-trimethylenenon-1-en-6-ynyl]-bicyclo[3.3.0]octan-3-ylidene]ethan-1-ol in yields 140 mg of the title compound as a colorless oil.

IR: 3600, 3410 (broad), 2932, 1732, 1600, 972 cm$^{-1}$.

The starting material for the above title compound is produced as set forth below:

18(a)

(2-[(E)-1S,5S,6R,7R)-7-Tetrahydropyran-2-yloxy)-6-[(E)-(3R)-3-tetrahydropyran-2-yloxy)4,4-trimethylenenon-1en-6-ynyl]-bicyclo[3.3.0]octan-3-ylidene]ethan-1-ol In analogy to Example 15(a), 2.1 g of (1R,5S,6R,7R)-7-(tetrahydropyran-2-yloxy)-6-[(E)-(3R)-3-tetrahydropyran-2-yloxy)4,4-trimethylenenont-1en-6-ynyl]-bicyclo[3.3.0]octan-3-one yields, after separation of isomers by chromatography, as the less polar compound 0.6 g of (2-[(Z)-1S,5S,6R,7R)-7-Tetrahydropyran-2-yloxy)-6-[(E)-(3R)-3-tetrahydropyran-2-yloxy)4,4-trimethylenenon-1en-6-ynyl]-bicyclo[3.3.0]octan-3-ylidene]ethan-1-ol and 0.65 g of the title compound as colorless oils.

IR: 3600, 3420, 2942, 2865, 1600, 972 cm$^{-1}$.

EXAMPLE 19

(5E)-13,14-Didehydro-20-methyl-3-oxa-18,18,19,19-tetrahydro-16,16-trimethylene-6a-carbaprostaglandin I$_2$ In analogy to Example 15, 200 mg of 2[(E)-(1S,5S,6R,7R)-7-(tetrahydropyran-2-yloxy)-6-[(3S)-3-(tetrahydropyran-2-yloxy)-4,4-trimethylenenona-1,6-diynyl]bicyclo[3.3.0]octan-3-ylidene]ethan-1-ol yields 89 mg of the title compound as a colorless oil.

IR: 3600, 3406 (broad), 2930, 2862, 2221, 1730, 1600 cm$^{-1}$.

19(a)

(2-[(E)-1S,5S,6R,7R)-7-Tetrahydropyran-2-yloxy)-6-[(3S)-3-tetrahydropyran-2-yloxy)4,4-trimethylenenona-1,6-diynyl]-bicyclo[3.3.0]octan-3-ylidene]ethan-1-ol In analogy to Example 15(a), 1.50 g of (1R,5S,6R,7R)-7-(tetrahydropyran-2-yloxy)-6-[(3S)-3-tetrahydropyran-2-yloxy)4,4-trimethylenenont-1,6-diynyl]-bicyclo[3.3.0]octan-3-one yields 420 mg of (2-[(Z)-1S,5S,6R,7R)-7-Tetrahydropyran-2-yloxy)-6-

[(3S)-3-tetrahydropyran-2-yloxy)4,4-trimethylenenona-1,6-diynyl]-bicyclo[3.3.0]octan-3-ylidene]ethan-1-ol as the less polar compound. As the more polar compound, 820 mg of the title compound is obtained as a colorless oil.

IR: 3600, 3420, 2948, 2862, 2225, 1600 cm$^{-1}$.

EXAMPLE 20

(5E)-18,19-Didehydro-19-methyl-3-oxa-16,16-trimethylene-6a-carbaprostaglandin $I_2$ In analogy to Example 15, 250 mg of 2[(E)-(1 S,5S,6R,7R)-7-(tetrahydropyran-2-yloxy)-6-[(3R)-3-(tetrahydropyran-2-yloxy)-4,4-trimethylenenocta-1,6-diynyl]bicyclo[3.3.0]octan-3-ylidene]ethan-1-ol yields 110 mg of the title compound as a colorless oil.

IR: 3600, 3415 (broad), 2942, 2860, 1734, 1601, 976 cm$^{-1}$.

20(a)

(2-[(E)-1S,5S,6R,7R)-7-Tetrahydropyran-2-yloxy)-6-[(3R)-3-tetrahydropyran-2-yloxy)4,4-trimethylenenocta-1,6-diynyl]-bicyclo[3.3.0]octan-3-ylidene]ethan-1-ol Analogously to Example 15(a), 3 g of (1R,5S,6R,7R)-7-(tetrahydropyran-2-yloxy)-6-[(3R)-7-methyl-(tetrahydropyran-2-yloxy)4,4-trimethylenenocta-1,6-diynyl]-bicyclo[3.3.0]octan-3-one yields, as the more polar compound, 1.60 g of the title compound as a colorless oil.

IR: 3600, 3410, 2938, 2858, 1160, 1015, 974 cm$^{-1}$.

EXAMPLE 21

(5E)-13,14-Didehydro-20-methyl-3-oxa-18,18,19,19-tetrahydro-16,16-trimethylene-6a-carbaprostaglandin $I_2$ Methyl Ester At 0° C., an etheral diazomethane solution is added dropwise to a solution of 100 mg of (5E)-13,14-didehydro-20-methyl-3-oxa-18,18,19,19-tetrahydro-16,16-trimethylene-6a-carbaprostaglandin $I_2$ (see Example 5) in 20 ml of dichloromethane + 5 ml of dimethoxyethane until the yellow coloration of the solution is permanent. The mixture is evaporated under vacuum and the residue purified by chromatography on silica gel with dichloromethane/2% isopropanol, thus obtaining 80 mg of the title compound as a colorless oil.

IR: 3600, 2942, 2860, 2228, 1742, 1135 cm$^{-1}$.

EXAMPLE 22

(5E)-3-Oxa-18,18,19,19-tetrahydro-16,16-trimethylene-6a-carbaprostaglandin $I_2$ Acetylamide 63 mg of triethylamine and thereafter, at 0° C., a solution of 48 mg of acetylisocyanate in 2 ml of acetonitrile are added to a solution of 255 mg of (5E)-3-Oxa-18,18,19,19-tetrahydro-16,16-trimethylene-6a-carbaprostaglandin $I_2$ 11,15-bis(tetrahydropyranyl ether) (see Example 15) in 5 ml of acetonitrile. After 2 hours at 20° C., the mixture is concentrated under vacuum, diluted with 100 ml of citrate buffer (pH 5), extracted with dichloromethane, the extract is washed in succession with sodium bicarbonate solution and brine, dried over magnesium sulfate, and evaporated under vacuum. To split off the blocking groups, the residue is stirred for 18 hours with 10 ml of glacial acetic acid/water/tetrahydrofuran (65/35/10) and evaporated under vacuum. The residue is chromatographed on silica gel with dichloromethane/3% isopropanol, thus obtaining 105 mg of the title compound as a colorless oil.

IR: 3600, 3500, 3410, 2950, 2862, 1725, 1138, 976 cm$^{-1}$.

EXAMPLE 23

(5E)-3-Oxa -20-methyl-18,18,19,19-tetrahydro-16,16-trimethylene-6a-carbaprostaglandin $I_2$ Carboxamide At 0° C., 65 mg of triethylamine and 90 mg of chloroformic acid isobutyl ester are added to a solution of 196 mg of (5E)-3-Oxa -20-methyl-18,18,19,19-tetrahydro-16,16-trimethylene-6a-carbaprostaglandin $I_2$ in 5 ml of dimethylformamide. After one hour, dry gaseous ammonia is conducted into the solution for 15 minutes and then the solution is allowed to stand for 2 hours at 0° C. For working up purposes, the mixture is diluted with citrate buffer (pH 5), extracted with ethyl acetate, washed with sodium bicarbonate solution and brine, dried over magnesium sulfate, and evaporated under vacuum. After chromatography of the residue on silica gel with dichloromethane/2% isopropanol, 150 mg of the title compound is obtained as a colorless oil.

IR: 3600, 3495, 3410, 2955, 2868, 1662, 1135, 976 cm$^{-1}$.

EXAMPLE 24

(5E)-13,14-Didehydro-20-methyl-3-oxa-18,18,19,19-tetrahydro-16,16-trimethylene-6a-carbaprostaglandin $I_2$ (2,3-Dihydroxypropyl)amide At 0° C., 59 mg of triethylamine and 80 mg of chloroformic acid isobutyl ester are added to a solution of 192 mg of (5Z)-13,14-didehydro-20-methyl-3-oxa-18,18,19,19-tetrahydro-16,16-trimethylene-6a-carbaprostaglandin $I_2$ in 4 ml of acetone. After 30 minutes, the mixture is combined with 240 mg of 1-amino-2,3-dihydroxypropane, 3 ml of acetone and 5 ml of acetonitrile, maintained for 2 hours at 20° C., concentrated under vacuum, diluted with 100 ml of dichloromethane, shaken with brine, dried over magnesium sulfate, and evaporated under vacuum. After chromatography of the residue on silica gel with methylene chloride/20% isopropanol, 150 mg of the title compound is obtained as a colorless oil.

IR: 3600, 3420 (broad), 2952, 2865, 2221, 1653, 1135, 1030 cm$^{-1}$.

EXAMPLE 25

(5E)-13,14-Dihydro-20-methyl-3-oxa-18,18,19,19-tetrahydro-16,16-trimethylene-6a-carbaprostaglandin $I_2$ Phenacyl Ester 200 mg of (5E)-13,14-didehydro-20-methyl-3-oxa-18,18,19,19-tetrahydro-16,16-trimethylene-6a-carbaprostaglandin $I_2$ is dissolved in 8 ml of acetone, combined with 150 mg of ω-bromoacetophenone and 2 ml of triethylamine, and stirred overnight at room temperature. The mixture is combined with 200 ml of ether, shaken in succession with water and brine, dried over magnesium sulfate, and evaporated under vacuum. The residue is purified by chromatography on silica gel with dichloromethane/2% acetone, thus obtaining 190 mg of the title compound.

IR: 3600, 2950, 2866, 2225, 1748, 1708, 1138, 1028 cm$^{-1}$.

EXAMPLE 26

(5E)-2-Decarboxy-13,14-didehydro-20-methyl-3-oxa-2-(2-oxazolin-2-yl)-18,18,19,19-tetrahydro-16,16-trimethylene-6a-carbaprostaglandin $I_2$ 180 mg of (5E)-13,14-didehydro-20-methyl-3-oxa-18,18,19,19-tetrahydro-16,16-trimethylene-6a-carbaprostaglandin $I_2$ is dissolved in 5 ml of hexamethyldisilazane and heated for 90 minutes to 140° C.; then the excess regent is distilled off under vacuum. The residue is dissolved in 5 ml of acetonitrile, combined with 786 mg of triphenylphosphine and 1 ml of trietylamine, and, at 0° C., 0.5 ml of a 1-molar solution of ethanolamine in acetonitrile is added dropwise thereto. After 18 hours at 20° C., the mixture is concentrated under vacuum and the residue washed five times with respectively 75 ml of hexane. The thus-formed crystals are separated from the oily residue, and the oily residue is dissolved in 15 ml of methanol, combined at 0° C. with 5 ml of 2N sodium hydroxide solution, and stirred for 30 minutes at 20° C. After concentration under vacuum to about 5 ml, the mixture is combined with 10 ml of water and extracted four times with respectively 10 ml of ethyl acetate. After drying over magnesium sulfate and evaporation, an oily residue is obtained which is chromatographed on silica gel with dichloromethane/2% isopropanol, thus obtaining 100 mg of the title compound as an oil.

EXAMPLE 27

(5E)-13,14-Didehydro-20-methyl-3-oxa-18,18,19,19-tetrahydro-16,16-trimethylene-6a-carbaprostaglandin $I_2$ Tris(hydroxymethyl)aminomethane Salt At 70° C., a solution of 60 mg of tris(hydroxymethyl)-aminomethane in 0.2 ml of water is added to a solution of 168 mg of (5E)-13,14-didehydro-20-methyl-3-oxa-18,18,19,19-tetrahydro-16,16-trimethylene-6a-carbaprostaglandin $I_2$ in 34 ml of acetonitrile. The mixture is allowed to cool under stirring, decanted from the solvent after 16 hours, and the residue dried under vacuum, thus isolating 145 mg of the title compound as a waxy mass.

We claim:
1. A carbacyclin derivative of the formula:

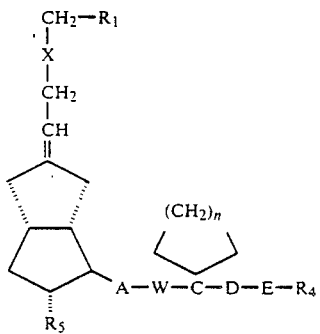

wherein
$R_1$ is $CH_2OH$ or

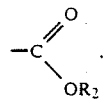

wherein $R_2$ is hydrogen; $C_1$–10alkyl; $C_1$–10alkyl substituted by halogen, $C_1$–4alkoxy, $C_6$–10aryl, substituted $C_6$–10aryl as defined below, di-$C_1$–4-alkylamino or tri-$C_1$–4-alkylammonium; $C_4$–10cycloalky; $C_4$–10cycloalkyl substituted by $C_1$–4-alkyl; $C_6$–10aryl; $C_6$–10aryl substituted by 1–3 halogen atoms, a phenyl group, 1–3 alkyl groups of 1–4 carbon atoms each, or a chloromethyl, fluoromethyl, trifluoromethyl, carboxy, hydroxy or alkoxy groups of 1–4 carbon atoms,

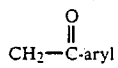

wherein aryl is a $C_6$–10aryl, or substituted $C_6$–10aryl as defined above; or a 5- or 6-membered aromatic heterocycle containing one O, N or S atom, all other atoms being C-atoms; or
$R_1$ is

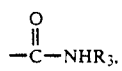

wherein $R_3$ is $C_1$–10alkanoyl or alkanesuylfonyl or $R_2$; or
$R_1$ is

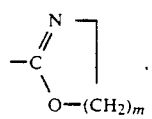

wherein m is 1 or 2;
X is $CH_2$,
A is trans-$CH=CH$— or —$C\equiv C$—;
W is a free or functionally modified hydroxymethylene group wherein the hydroxy group can be in the α- or β-position, wherein the term "functionally modified" refers to replacement of the H-atom on the hydroxy group with an acyl group of $C_1$–15 hydrocarbon carboxcylic or sulfonic acid or tetrahydropyranyl, tetrahydrofuranyl, α-ethoxyethyl, trimethylsilyl, dimethyl-tert-butylsilyl; or tri-p-benzylsilyl;
n is 1, 2, or 3;
D is a straight-chain alkylene group of 1–5 carbon atoms;
E is a —$C\equiv C$-bond or a —$CR_6=CR_7$-group wherein $R_6$ and $R_7$ are different from each other and are either (H; $C_{1-5}$ alkyl) or (H; halo);
$R_4$ is $C_{1-10}$ alkyl; $C_{1-10}$ alkyl substituted as defined above; $C_{4-10}$-cycloalkyl; $C_{4-10}$-cycloalkyl substituted as defined above; $C_{6-10}$-aryl; $C_{6-10}$-aryl substituted as defined above; or a 5 or 6-member aromatic heterocycle containing one O, N or S-atom, all other atoms being C-atoms;
$R_5$ is a free or functionally modified hydroxy group as defined above;

or if $R_2$ means a hydrogen atom, a physiologically compatible salt thereof with a base.

2. (5E)-18,18,19,19-Tetrahydro-16,16-trimethylene-6a-carbaprostaglandin $I_2$, a compound of claim 1.

3. (5E)-13,14-Didehydro-18,18,19,19-tetrahydro-16,16-trimethylene-6a-carbaprostaglandin $I_2$, a compound of claim 1.

4. (5E)-20-Methyl-18,18,19,19-tetrahydro-16,16-trimethylene-6a-carbaprostaglandin $I_2$, a compound of claim 1.

5. (5E)-20-Ethyl-18,18,19,19-tetrahydro-16,16-trimethylene-6a-carbaprostaglandin $I_2$, a compound of claim 1.

6. (5E)-13,14-Didehydro-20-methyl-18,18,19,19-tetrahydro-16,16-trimethylene-6a-carbaprostaglandin $I_2$, a compound of claim 1.

7. (5E)-13,14-Didehydro-20-methyl-18,18,19,19-tetrahydro-16,16-trimethylene-6a-carbaprostaglandin $I_2$, a compound of claim 1.

8. (5E)-20-Ethyl-13,14-didehydro-18,18,19,19-tetrahydro-16,16-trimethylene-6a-carbaprostaglandin $I_2$, a compound of claim 1.

9. (5E)-20-Methyl-19,19,20,20-tetrahydro-16,16-trimethylene-6a-carbaprostaglandin $I_2$, a compound of claim 1.

10. (5E)-13,14-Didehydro-20-methyl-19,19,20,20-tetrahydro-16,16-trimethylene-6a-carbaprostaglandin $I_2$, a compound of claim 1.

11. (5E)-18,18,19,19-Tetrahydro-16,16-trimethylene-6a-carbaprostaglandin $I_2$, a compound of claim 1.

12. (5E)-18,19-Didehydro-19-methyl-16,16-trimethylene-6a-carbaprostaglandin $I_2$, a compound of claim 1.

13. (5E)-18,18,19,19-Tetrahydro-16,16-trimethylene-N-methanesulfonyl-6a-carbaprostaglandin $I_2$ Carboxamide, a compound of claim 1.

14. (5E)-13,14-Didehydro-18,18,19,19-tetrahydro-16,16-trimethylene-6a-carbaprostaglandin $I_2$ Carboxamide, a compound of claim 1.

15. (5E)-18,19-Didehydro-19-chloro-16,16-trimethylene-6a-carbaprostaglandin $I_2$, a compound of claim 1.

16. A compound of claim 1 wherein E is $-C\equiv C-$.

17. A compound of claim 16 wherein n is 1.

18. A compound of claim 1 wherein E is $-C\equiv C-$.

19. A compound of claim 18 wherein n is 1.

20. A compound of claim 1 wherein
$R_1$ is $CH_2OH$.

21. A pharmaceutical composition comprising an amount of a compound of claim 1 effective to inhibit thrombocyte aggregation in a patient and a pharmaceutically acceptable carrier.

22. A pharmaceutical composition of claim 21 wherein the amount of active ingredient is 0.01 to 100 mg.

23. A method of inhibiting thrombocyte aggregation in a patient in need of such treatment, comprising administering a compound of claim 1.

* * * * *

UNITED STATES PATENT AND TRADEMARK OFFICE
CERTIFICATE OF CORRECTION

PATENT NO. : 5,124,343

DATED : June 23, 1992

INVENTOR(S) : Helmut VORBRUEGGEN et al

It is certified that error appears in the above-indentified patent and that said Letters Patent is hereby corrected as shown below:

Please delete in col. 32, lines 6-29 and replace with the attached sheet.

UNITED STATES PATENT AND TRADEMARK OFFICE
CERTIFICATE OF CORRECTION

PATENT NO. : 5,124,343
DATED : June 23, 1992
INVENTOR(S) : Helmut VORBRUEGGEN et al It is certified that error appears in the above-indentified patent and that said Letters Patent is hereby corrected as shown below:

-- wherein $R_2$ is hydrogen; $C_{1-10}$ alkyl; $C_{1-10}$ alkyl substituted by halogen, $C_{1-4}$ alkoxy, $C_{6-10}$ aryl, substituted $C_{6-10}$ aryl as defined below, di-$C_{1-4}$ alkylamino or tri-$C_{1-4}$-alkylammonium; $C_4$-$C_{10}$ cycloalkyl; $C_4$-$C_{10}$ cycloalkyl substituted by $C_{1-4}$-alkyl; $C_{6-10}$ aryl; $C_{6-10}$ aryl substituted by 1-3 halogen atoms, a phenyl group, 1-3 alkyl groups of 1-4 carbon atoms each, or a chloromethyl, fluoromethyl, trifluoromethyl, carboxy, hydroxy or alkoxy group of 1-4 carbon atoms;

$$CH_2-C-aryl$$

wherein aryl is a $C_{6-10}$ aryl, or substituted $C_{6-10}$ aryl as defined above; or a 5- or 6-membered aromatic heterocycle containing one O, N or S atom, all other atoms being C-atoms; or $R_1$ is $-C-NHR_3$, wherein $R_3$ is $C_{1-10}$ alkanoyl or alkanesulfonyl or --.

Signed and Sealed this

Twenty-first Day of September, 1993

Attest:

BRUCE LEHMAN

Attesting Officer

Commissioner of Patents and Trademarks